United States Patent [19]
Dyer et al.

[11] Patent Number: 5,387,207
[45] Date of Patent: Feb. 7, 1995

[54] THIN-UNIT-WET ABSORBENT FOAM MATERIALS FOR AQUEOUS BODY FLUIDS AND PROCESS FOR MAKING SAME

[75] Inventors: John C. Dyer; Thomas A. DesMarais, both of Cincinnati; Gary D. LaVon, Harrison; Keith J. Stone, Fairfield; Gregory W. Taylor, West Chester; Gerald A. Young, Cincinnati, all of Ohio

[73] Assignee: The Procter & Gamble Company, Cincinnati, Ohio

[21] Appl. No.: 989,270

[22] Filed: Dec. 11, 1992

Related U.S. Application Data

[60] Continuation-in-part of Ser. No. 743,838, Aug. 12, 1991, abandoned, Ser. No. 743,839, Aug. 12, 1991, Pat. No. 5,260,345, Ser. No. 743,951, Aug. 12, 1991, Pat. No. 5,352,711, and Ser. No. 935,935, Aug. 27, 1992, Pat. No. 5,198,472, which is a division of Ser. No. 830,159, Feb. 3, 1992, Pat. No. 5,149,720, which is a continuation-in-part of Ser. No. 743,947, Aug. 12, 1991, abandoned, and a continuation-in-part of Ser. No. 935,938, Aug. 27, 1992, Pat. No. 5,318,554, which is a continuation of Ser. No. 743,950, Aug. 12, 1991, Pat. No. 5,147,345.

[51] Int. Cl.$^6$ ...................... A61F 13/15; A61F 13/20
[52] U.S. Cl. ................... 604/369; 604/358; 604/372; 604/367; 521/64
[58] Field of Search ............... 604/358, 369, 359, 360, 604/367, 372–375, 378; 521/62–64

[56] References Cited

U.S. PATENT DOCUMENTS

| | | |
|---|---|---|
| 3,255,127 | 6/1966 | von Bonin et al. |
| 3,431,911 | 3/1969 | Meisel, Jr. |
| 3,563,243 | 2/1971 | Lindquist |
| 3,565,817 | 2/1971 | Lissant |
| 3,673,142 | 6/1972 | Saunders et al. |
| 3,734,867 | 5/1973 | Will |
| 3,763,056 | 10/1973 | Will |
| 3,806,474 | 4/1974 | Blair |
| 3,896,823 | 7/1975 | Spatz |
| 3,915,726 | 10/1975 | Hansen et al. |
| 3,988,508 | 10/1976 | Lissant |
| 3,992,333 | 11/1976 | Emmons et al. |
| 4,076,656 | 2/1978 | White et al. |
| 4,102,340 | 7/1978 | Mesek et al. |

(List continued on next page.)

FOREIGN PATENT DOCUMENTS

| | | |
|---|---|---|
| 2017570 | 11/1990 | Canada |
| 299122 | 1/1989 | European Pat. Off. |
| 299762 | 1/1989 | European Pat. Off. |
| 397110 | 11/1990 | European Pat. Off. |
| 399564 | 11/1990 | European Pat. Off. |
| 410480A2 | 1/1991 | European Pat. Off. |

(List continued on next page.)

OTHER PUBLICATIONS

Structure of High–Internal–Phase–Ratio Emulsions, K. J. Lissant et al, Journal of Colloid and Interface Science, vol. 47, No. 2, May 1974, pp. 416–423.

A study of Medium and High Internal Phase Ratio Water/Polymer Emulsions; K. J. Lissant et al, Journal of Colloid and Interface Science, vol. 42, No. 1, Jan. 1973, pp. 201–208.

The Geometry of High–Internal–Phase–Ratio Emulsions, K. J. Lissant, Journal of Colloid and Interface Science, vol. 22 (1966), pp. 462–468.

Low–density, microcellular polystyrene foams, J. H.

(List continued on next page.)

Primary Examiner—Randall L. Green
Assistant Examiner—P. Zuttarelli
Attorney, Agent, or Firm—Eric W. Guttag; E. Kelly Linman

[57] ABSTRACT

Relatively thin, collapsed, i.e. unexpanded, polymeric foam materials that, upon contact with aqueous body fluids, expand and absorb such fluids, are disclosed. A process for consistently obtaining such relatively thin, collapsed polymeric foam materials by polymerizing a specific type of water-in-oil emulsion, commonly known as High Internal Phase Emulsions or "HIPE", is also disclosed.

23 Claims, 8 Drawing Sheets

U.S. PATENT DOCUMENTS

| | | |
|---|---|---|
| 4,394,930 | 7/1983 | Korpman . |
| 4,432,920 | 2/1984 | Ishikawa et al. . |
| 4,473,611 | 9/1984 | Haq . |
| 4,522,953 | 6/1985 | Barby et al. . |
| 4,554,297 | 11/1985 | Dabi . |
| 4,603,069 | 7/1986 | Haq et al. . |
| 4,606,958 | 8/1986 | Haq et al. . |
| 4,611,014 | 9/1986 | Jomes et al. . |
| 4,612,334 | 9/1986 | Jones et al. . |
| 4,636,209 | 1/1987 | Lassen . |
| 4,659,564 | 4/1987 | Cox et al. . |
| 4,668,709 | 5/1987 | Jones et al. . |
| 4,673,402 | 6/1987 | Weisman et al. . |
| 4,675,213 | 6/1987 | Yamamori et al. . |
| 4,699,619 | 10/1987 | Bernardin . |
| 4,699,620 | 10/1987 | Bernardin . |
| 4,788,225 | 11/1988 | Edwards et al. ............... 521/64 |
| 4,797,310 | 1/1989 | Barby et al. . |
| 4,798,603 | 1/1989 | Meyer et al. . |
| 4,822,453 | 4/1989 | Dean et al. . |
| 4,839,395 | 6/1989 | Masamizu et al. . |
| 4,888,093 | 12/1989 | Dean et al. . |
| 4,888,231 | 12/1989 | Angstadt . |
| 4,889,595 | 12/1989 | Herron et al. . |
| 4,889,596 | 12/1989 | Schoggen et al. . |
| 4,889,597 | 12/1989 | Bourbon et al. . |
| 4,898,642 | 2/1990 | Moore et al. . |
| 4,935,022 | 6/1990 | Lash et al. . |
| 4,957,810 | 9/1990 | Eleouet et al. . |
| 4,985,467 | 1/1991 | Kelly et al. . |
| 4,988,344 | 1/1991 | Reising et al. . |
| 4,988,345 | 1/1991 | Reising . |
| 4,994,037 | 2/1991 | Bernardin . |
| 5,009,650 | 4/1991 | Bernardin . |
| 5,147,345 | 9/1992 | Young et al. . |
| 5,149,720 | 9/1992 | DesMarais et al. . |
| 5,198,472 | 3/1993 | DesMarais et al. . |
| 5,250,576 | 10/1993 | DesMarais et al. . |
| 5,260,345 | 11/1993 | DesMarais et al. ............... 521/92 |
| 5,268,224 | 12/1993 | DesMarais et al. . |
| 5,292,777 | 3/1994 | DesMarias et al. . |

FOREIGN PATENT DOCUMENTS

| | | |
|---|---|---|
| 427317A2 | 5/1991 | European Pat. Off. . |
| 440472A1 | 8/1991 | European Pat. Off. . |
| 2659341 | 9/1991 | France . |
| 53-062138 | 6/1978 | Japan . |
| 61-072003 | 4/1986 | Japan . |
| 86-160429-25 | 5/1986 | Japan . |
| 2-239863 | 9/1990 | Japan . |
| 2-289608 | 11/1990 | Japan . |
| 3-49759 | 3/1991 | Japan . |
| 1493356 | 11/1977 | United Kingdom . |
| 2078527 | 1/1982 | United Kingdom . |
| 2194166A | 8/1986 | United Kingdom . |
| WO84/00015 | 1/1984 | WIPO . |
| WO92/19445 | 11/1992 | WIPO . |

OTHER PUBLICATIONS

Aubert and R. L. Clough, Polymer, 1985, vol. 26, Dec., pp. 2047-2054.

New melamine-based elastic foam, H. Weber & F. Kruckau, Special reprint from "Kunststoffe German plastics" 1985/11 (6 pages).

Preparation of multishell ICF target plastic foam cushion materials by thermally induced phase inversion processes, A. T. Young et al, J. Vac. Sci. Technol., 20(4), Apr. 1982, pp. 1094–1097.

Mechanical Structure–Property Relationships of Microcellular, Low Density Foams, J. D. Lemay, Mat. Res. Soc. Symp. Proc. vol. 207, 1991 Materials Research Society, pp. 21–26.

Cellular Solids, Structure & Properties, The Mechanics of Foams: Basic Results, Lorna J. Gibson/Michael F. Ashby, Pergamon Press, pp. 120–200.

THIN-UNIT-WET ABSORBENT FOAM MATERIALS FOR AQUEOUS BODY FLUIDS AND PROCESS FOR MAKING SAME

CROSS REFERENCE TO RELATED APPLICATIONS

This application is a continuation-in-part of U.S. application Ser. Nos. 743,838 now abandoned, 743,839 now U.S. Pat. No. 5,260,345 and 743,951 now U.S. Pat. No. 5,352,511, all filed Aug. 12, 1991, and U.S. application Ser. No. 935,935 now U.S. Pat. No. 5,198,472, filed Aug. 27, 1992, which is a divisional of U.S. application Ser. No. 830,159 now U.S. Pat. No. 5,149,720, filed Feb. 3, 1992, which is a continuation-in-part of U.S. application Ser. No. 743,947, filed Aug. 12, 1991 (now abandoned), and U.S. application Ser. No. 935,938 now U.S. Pat. No. 5,318,554, filed Aug. 27, 1992, which is a continuation of U.S. application Ser. No. 743,950, filed Aug. 12, 1991 (now U.S. Pat. No. 5,147,345, issued Sep. 15, 1992).

FIELD OF THE INVENTION

This application relates to flexible, microporous, open-celled polymeric foam materials having fluid absorption and retention characteristics that make them particularly suitable for absorbing aqueous body fluids, e.g., urine. This application particularly relates to absorbent foam materials that remain relatively thin until wetted with such fluids.

BACKGROUND OF THE INVENTION

The development of highly absorbent articles for use as disposable diapers, adult incontinence pads and briefs, and catamenial products such as sanitary napkins, are the subject of substantial commercial interest. A highly desired characteristic for such products is thinness. For example, thinner diapers are less bulky to wear, fit better under clothing, and are less noticeable. They are also more compact in the package, making the diapers easier for the consumer to carry and store. Compactness in packaging also results in reduced distribution costs for the manufacturer and distributor, including less shelf space required in the store per diaper unit.

The ability to provide thinner absorbent articles such as diapers has been contingent on the ability to develop relatively thin absorbent cores or structures that can acquire and store large quantities of discharged body fluids, in particular urine. In this regard, the use of certain particulate absorbent polymers often referred to as "hydrogels," "superabsorbents" or "hydrocolloid" materials has been particularly important. See, for example, U.S. Pat. No. 3,699,103 (Harper et al), issued Jun. 13, 1972, and U.S. Pat. No. 3,770,731 (Harmon), issued Jun. 20, 1972, that disclose the use of such particulate absorbent polymers in absorbent articles. Indeed, the development of thinner diapers has been the direct consequence of thinner absorbent cores that take advantage of the ability of these particulate absorbent polymers to absorb large quantities of discharged aqueous body fluids, typically when used in combination with a fibrous matrix. See, for example, U.S. Pat. No. 4,673,402 (Weisman et al), issued Jun. 16, 1987 and U.S. Pat. No. 4,935,022 (Lash et al), issued Jun. 19, 1990, that disclose dual-layer core structures comprising a fibrous matrix and particulate absorbent polymers useful in fashioning thin, compact, nonbulky diapers.

These particulate absorbent polymers are unsurpassed in their ability to retain large volumes of fluids, such as urine. A representative example of such particulate absorbent polymers are lightly crosslinked polyacrylates. Like many of the other absorbent polymers, these lightly crosslinked polyacrylates comprise a multiplicity of anionic (charged) carboxy groups attached to the polymer backbone. It is these charged carboxy groups that enable the polymer to absorb aqueous body fluids as the result of osmotic forces.

Besides osmotic forces, absorbency based on capillary forces is also important in many absorbent articles, including diapers. Capillary forces are notable in various everyday phenomena, as exemplified by a paper towel soaking up spilled liquids. Capillary absorbents can offer superior performance in terms of the rate of fluid acquisition and wicking, i.e. the ability to move aqueous fluid away from the point of initial contact. Indeed, the dual-layer core absorbent structures noted above use the fibrous matrix as the primary capillary transport vehicle to move the initially acquired aqueous body fluid throughout the absorbent core so that it can be absorbed and retained by the particulate absorbent polymer positioned in layers or zones of the core.

An alternative absorbent material potentially capable of providing capillary fluid transport would be open-celled polymeric foams. If made appropriately, open-celled polymeric foams could provide features of capillary fluid acquisition, transport and storage required for use in high performance absorbent cores for absorbent articles such as diapers. Absorbent articles containing such foams could possess desirable wet integrity, could provide suitable fit throughout the entire period the article is worn, and could avoid degradation in shape during use. In addition, absorbent articles containing such foam structures could be easier to manufacture on a commercial scale. For example, absorbent diaper cores could simply be stamped out of continuous foam sheets and could be designed to have considerably greater integrity and uniformity than air-laid fibrous absorbent cores containing particulate absorbent polymers. Such foams could also be molded in any desired shape, or even formed into integral, unitary diapers.

Literature and commercial practice is replete with descriptions of various types of polymeric foams that can imbibe a variety of fluids for a variety of purposes. Indeed, employment of certain types of polymeric foam materials as elements of absorbent articles such as diapers and catamenial products has previously been suggested. See, for example, U.S. Pat. No. 4,029,100 (Karami), issued Jun. 14, 1977, that discloses a shape-retaining diaper that can employ a foam element in the crotch area of its absorbent pad assembly in order to provide high wet resiliency. Certain types of polymeric foam materials have also been suggested as useful in absorbent articles for the purpose of actually imbibing, wicking and/or retaining aqueous body fluids. See, for example, U.S. Pat. No. 3,563,243 (Lindquist), issued Feb. 6, 1971 (absorbent pad for diapers and the like where the primary absorbent is a hydrophilic polyurethane foam sheet); U.S. Pat. No. 4,554,297 (Dabi), issued Nov. 19, 1985 (body fluid absorbing cellular polymers that can be used in diapers or catamenial products); U.S. Pat. No. 4,740,528 (Garvey et al), issued Apr. 26, 1988 (absorbent composite structures such as diapers, feminine care products and the like that contain sponge absorbents made from certain types of super-wicking, crosslinked polyurethane foams).

Although various polymeric foam materials have been suggested for use in absorbent articles, there is still a need for absorbent foam materials having optimized combinations of features and characteristics that would render such foams especially useful in commercially marketed absorbent products such as diapers. In terms of desired absorbency characteristics, including capillary fluid transport capability, it has been determined that optimized absorbent, open-celled polymeric foams should have the following characteristics:

(a) a relatively greater affinity for absorbing body fluids than exhibited by other components in the absorbent article so that the foam material can drain (partition) fluids from these other components and keep the fluids stored within the foam structure;

(b) relatively good wicking and fluid distribution characteristics in order for the foam to transport the imbibed urine or other body fluid away from the initial impingement zone and into the unused balance of the foam structure, thus allowing for subsequent gushes of fluid to be accommodated; and (c) a relatively high storage capacity with a relatively high fluid capacity under load, i.e. under compressive forces.

As previously noted, a thinner absorbent core is usually a requirement for making relatively thin absorbent articles, such as diapers. However, providing absorbent polymeric foam materials that remain relatively thin in form until wetted with aqueous body fluids is not straightforward. The absorbent foam material needs to remain relatively thin during normal storage and use prior to being wetted. This relatively thin polymeric foam material must additionally have the needed absorbency characteristics described above if it is to be useful in high performance absorbent cores. Making relatively thin polymeric foams that are sufficiently soft and flexible for comfort of the wearer is also not a trivial task.

Accordingly, it would be desirable to be able to make an open-celled absorbent polymeric foam material that: (1) has adequate or preferably superior absorbency characteristics, including capillary fluid transport capability, so as to be desirable in high performance absorbent cores used in absorbent articles such as diapers, adult incontinence pads or briefs, sanitary napkins and the like; (2) is relatively thin during normal storage and use until wetted with aqueous body fluids; (3) is sufficiently flexible and soft so as to provide a high degree of comfort to the wearer of the absorbent article; and (4) can be manufactured on a commercial scale, at relatively reasonable or low cost.

DISCLOSURE OF THE INVENTION

The present invention relates to relatively thin, collapsed (i.e. unexpanded), polymeric foam materials that, upon contact with aqueous body fluids, expand and absorb such fluids. These absorbent polymeric foam materials comprise a hydrophilic, flexible, nonionic polymeric foam structure of interconnected open-cells that provides a specific surface area per foam volume of at least about 0.025 m$^2$/cc. The foam structure has incorporated therein at least about 0.1% by weight of a toxicologically acceptable, hygroscopic, hydrated salt. In its collapsed state, the foam structure has an expansion pressure of about 30,000 Pascals or less. In its expanded state, the foam structure has a density, when saturated at 88° F. (31.1° C.) to its free absorbent capacity with synthetic urine having a surface tension of 65±5 dynes/cm, of from about 10 to about 50% of its dry basis density in its collapsed state.

It is believed that the ability of the polymeric foams of the present invention to remain in a collapsed, unexpanded state is due to the capillary pressures developed within the collapsed foam structure that at least equals the force exerted by the elastic recovery tendency (i.e., expansion pressure) of the compressed polymer. Surprisingly, these collapsed polymeric foam materials remain relatively thin during normal shipping, storage and use conditions, until ultimately wetted with aqueous body fluids, at which point they expand. Because of their excellent absorbency characteristics, including capillary fluid transport capability, these collapsed polymeric foam materials are extremely useful in high performance absorbent cores for absorbent articles such as diapers, adult incontinence pads or briefs, sanitary napkins, and the like. These collapsed polymeric foam materials are also sufficiently flexible and soft so as to provide a high degree of comfort to the wearer of the absorbent article.

The present invention further relates to a process for consistently obtaining such relatively thin, collapsed polymeric foam materials by polymerizing a specific type of water-in-oil emulsion having a relatively small amount of an oil phase and a relatively greater amount of a water phase, commonly known in the art as High Internal Phase Emulsions or "HIPE." The oil phase of these HIPE emulsions comprises from about 67 to about 98% by weight of a monomer component having: (a) from about 5 to about 40% by weight of a substantially water-insoluble, monofunctional glassy monomer; (b) from about 30 to about 80% by weight of a substantially water-insoluble. monofunctional rubbery comonomer; (c) from about 10 to about 40% by weight of a substantially water-insoluble polyfunctional crosslinking agent component. The oil phase further comprises from about 2 to about 33% by weight of an emulsifier component that is soluble in the oil phase and will provide a stable emulsion for polymerization. The water or "internal" phase of these HIPE emulsions comprises an aqueous solution containing from about 0.2 to about 20% by weight of a water-soluble electrolyte. The weight ratio of the water phase to the oil phase in these HIPE emulsions ranges from about 12:1 to about 100:1. The polymerized foam is subsequently dewatered (with or without prior washing/treatment steps) to provide the collapsed foam material.

An important aspect of the process of the present invention is to carry out the emulsion formation and polymerization steps in a manner such that coalescence of the relatively small water droplets formed in the HIPE emulsion is reduced. This leads to a number average cell size in the resulting polymeric foam material of about 50 microns or less. It is believed that this reduction in coalescence of the relatively small water droplets formed in the HIPE emulsion, and the resulting smaller number average cell size in the polymeric foam material, is a key mechanism behind consistent formation of relatively thin, collapsed polymeric foam materials according to the present invention, and especially collapsed foam materials having good absorbency and fluid transport characteristics. This reduction in coalescence can be consistently achieved by the use of certain emulsifier systems, by the use of lower temperatures during polymerization (curing), or both, as described hereafter. Moreover, these relatively thin, collapsed absorbent polymeric foam materials can be consistently manufactured according to the process of the present invention on a potentially commercial scale, and at a potentially reasonable or low cost.

DETAILED DESCRIPTION OF THE INVENTION

Figure 1:
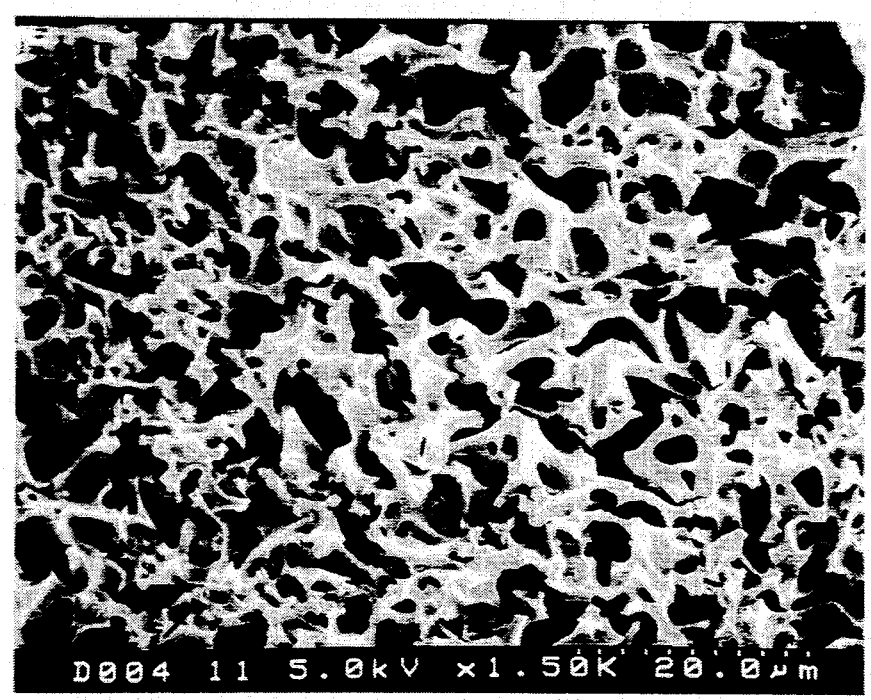
FIG. 1 of the drawings is a photomicrograph (1500X magnification) of an edge view of a cut section of a representative absorbent polymeric foam according to the present invention in its collapsed state.

Polymeric foams of the type referred to herein can be characterized as the structures which result when a relatively monomer-free liquid is dispersed as droplets or "bubbles" in a polymerizable monomer-containing liquid, followed by polymerization of the monomers in the monomer-containing liquid which surrounds the droplets. The resulting polymerized dispersion can be in the form of a porous solidified structure which is an aggregate of cells, the boundaries or walls of which cells comprise solid polymerized material. The cells themselves contain the relatively monomer-free liquid which, prior to polymerization, had formed the droplets in the liquid dispersion.

As described more fully hereafter, the collapsed polymeric foam materials useful as absorbents in the present invention are typically prepared by polymerizing a particular type of water-in-oil emulsion. Such an emulsion is formed from a relatively small amount of a polymerizable monomer-containing oil phase and a relatively larger amount of a relatively monomer-free water phase. The relatively monomer-free, discontinuous "internal" water phase thus forms the dispersed droplets surrounded by the continuous monomer-containing oil phase. Subsequent polymerization of the monomers in the continuous oil phase forms the cellular foam structure. The aqueous liquid remaining in the foam structure after polymerization can be removed by pressing, thermal drying and/or vacuum dewatering.

Polymeric foams, including foams prepared from water-in-oil emulsions, can be relatively closed-celled or relatively open-celled in character, depending upon whether and/or the extent to which, the cell walls or boundaries, i.e., the cell windows, are filled with, or void of, polymeric material. The polymeric foam materials useful in the absorbent articles and structures of the present invention are those which are relatively open-celled in that the individual cells of the foam are for the most part not completely isolated from each other by polymeric material of the cell walls. Thus the cells in such substantially open-celled foam structures have intercellular openings or "windows" which are large enough to permit ready fluid transfer from one cell to the other within the foam structure.

In substantially open-celled structures of the type useful herein, the foam will generally have a reticulated character with the individual cells being defined by a plurality of mutually connected, three dimensionally branched webs. The strands of polymeric material which make up the branched webs of the open-cell foam structure can be referred to as "struts." Open-celled foams having a typical strut-type structure are shown by way of example in the photomicrograph set forth as FIG. 2. For purposes of the present invention, a foam material is "open-celled" if at least 80% of the cells in the foam structure that are at least 1 micron size are in fluid communication with at least one adjacent cell. Alternatively, a foam material can be considered to be substantially open-celled if it has a measured available pore volume that is at least 80% of the theoretically available pore volume, e.g., as determined by the water-to-oil weight ratio of the HIPE emulsion from which the foam material is formed.

In addition to being open-celled, the collapsed polymeric foam materials of this invention are hydrophilic in character. The foams herein must be sufficiently hydrophilic to permit the foam to absorb aqueous body fluids in the amounts hereafter specified. As discussed hereafter with respect to preferred foam types and methods of foam preparation, the internal surfaces of the foam structures herein can be rendered hydrophilic by virtue of residual hydrophilizing agents left in the foam structure after polymerization or by virtue of selected post-polymerization foam treatment procedures which can be used to alter the surface energy of the material which forms the foam structure.

The extent to which polymeric foam structures such as those of this invention are "hydrophilic" can be quantified by referencing the "adhesion tension" exhibited by such foams in contact with an absorbable test liquid. Adhesion tension is defined by the formula $$AT = \gamma \cos \Theta$$

wherein AT is adhesion tension in dynes/cm;

$\gamma$ is the surface tension of a test liquid absorbed by the foam material in dynes/cm;

$\Theta$ is the contact angle in degrees between the surface of the polymeric foam and the vector which is tangent to the test liquid at the point that the test liquid contacts the foam surface.

For any given hydrophilic foam material, the adhesion tension exhibited by the foam can be determined experimentally using a procedure whereby weight uptake of a test liquid, e.g., synthetic urine, is measured for a foam sample of known dimensions and capillary suction specific surface area. Such a procedure is described in greater detail in the TEST METHODS section hereafter. The foams which are useful as absorbents in the present invention are generally those which have been rendered hydrophilic to the extent that they exhibit an adhesion tension of from about 15 to about 65 dynes/cm, more preferably from about 20 to about 65 dynes/cm, as determined by capillary suction uptake of synthetic urine having a surface tension of 65±5 dynes/cm.

In addition to being "open celled" and "hydrophilic," the polymeric foam materials useful in the present invention have a specific set of structural and mechanical properties, features and/or characteristics. It should be understood that these foam materials can have different properties, features and/or characteristics at different times prior to contact between the foam and the aqueous body fluid to be absorbed. For example, during their manufacture, shipping, storage, etc., the foams herein can have density and/or cell size values outside the ranges set forth hereafter for these parameters. However, such foams are nevertheless still within the scope of this invention if they later undergo physical or rheological changes so that they have the requisite values specified hereafter for these properties, features and/or characteristics at at least some point prior to and/or during contact with the aqueous body fluid to be absorbed.

The properties, features and/or characteristics of the polymeric foam materials of the present invention are somewhat interrelated and interdependent, but can be essentially categorized as follows: (I) those particularly relevant to its collapsed state; (II) those particularly relevant to its expanded state; (III) those equally relevant to either its collapsed or expanded state; and (IV) those particularly relevant to its absorbency when in contact with aqueous body fluids.

I. Collapsed State.

The collapsed polymeric foam materials of the present invention are usually obtained by polymerizing a HIPE-type emulsion as described hereafter. These are water-in-oil emulsions having a relatively small amount of an oil phase and a relatively greater amount of a water phase. Accordingly, after polymerization, the resulting foam contains a substantial amount of water. This water can be expressed from the foam by compressive forces, and/or can be reduced by thermal drying, such as by heating in an oven, or by vacuum dewatering. After compression, and/or thermal drying/vacuum dewatering, the polymeric foam material is in a collapsed, or unexpanded state.

Figure 2:
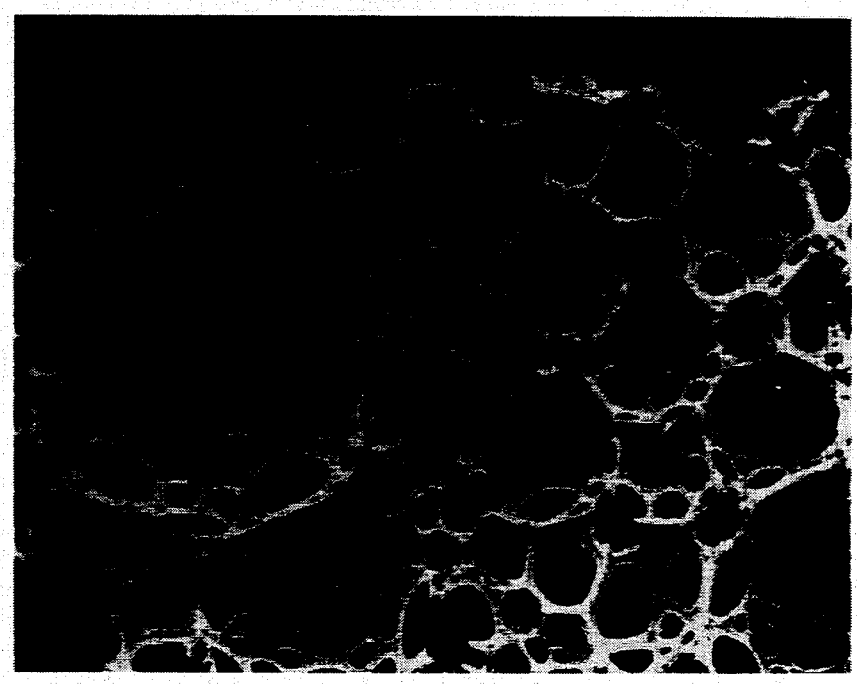
FIG. 2 of the drawings is a photomicrograph of a cut section of a representative absorbent polymeric foam according to the present invention in its expanded state.

The cellular structure of a representative collapsed HIPE foam from which water has been expressed by compression is shown in the photomicrograph set forth in FIG. 1. As shown in FIG. 1, the cellular structure of the foam is distorted, especially when compared to the HIPE foam structure shown in FIG. 2. (The foam structure shown in FIG. 2 is in its expanded state.) As can also be seen in FIG. 1, the voids or pores (dark areas) in the foam structure have been flattened or elongated. There is also no or minimal contact between adjacent struts of the foam structure.

Following compression and/or thermal drying/vacuum dewatering, the collapsed polymeric foam material can potentially re-expand, especially when wetted with aqueous body fluids. (See FIG. 2 which shows a typical HIPE foam structure according to the present invention in its expanded state.) Surprisingly, polymeric foam materials of the present invention remain in this collapsed, or unexpanded state, for significant periods of time, e.g., up to at least about 1 year. The ability of the polymeric foam materials of the present invention to remain in this collapsed/unexpanded state is believed to be due to the capillary forces, and in particular the capillary pressures developed within the foam structure. As used herein, "capillary pressure" refers to the pressure differential across the liquid/air interface due to the curvature of meniscus within the narrow confines of the pores in the foam. [See Chatterjee, "Absorbency," *Textile Science and Technology*, Vol. 7, 1985, p. 36.] For wetting liquids, this is essentially a pressure drop compared to atmospheric.

After compression, and/or thermal drying/vacuum dewatering, the polymeric foam material of the present invention has residual water that includes both the water of hydration associated with the hydroscopic, hydrated salt incorporated therein (as described hereafter), as well as free water absorbed within the foam. It is this residual water (assisted by the hydrated salts) that is believed to exert capillary pressures on the resulting collapsed foam structure. Collapsed polymeric foam materials of the present invention can have residual water contents of at least about 4%, typically from about 4 to about 30%, by weight of the foam when stored at ambient conditions of 72° F. (22° C.) and 50% relative humidity. Preferred collapsed polymeric foam materials of the present invention have residual water contents of from about 5 to about 15% by weight of the foam.

In its collapsed state, the capillary pressures developed within the foam structure at least equal the forces exerted by the elastic recovery or modulus of the compressed polymer. In other words, the capillary pressure necessary to keep the collapsed foam material relatively thin is determined by the countervaling force exerted by the compressed polymeric foam as it tries to "spring back." The elastic recovery tendency of polymeric foams can be determined from stress-strain experiments where the expanded foam is compressed to about 25% of its original, expanded caliper (thickness) and then held in this compressed state until an equilibrium or relaxed stress value is measured. Alternatively, and for the purposes of the present invention, the equilibrium relaxed stress value is determined from measurements on the polymeric foam in its collapsed state when in contact with aqueous fluids, e.g., water. This alternative relaxed stress value is hereafter referred to as the "expansion pressure" of the foam. A detailed description of a procedure for determining the expansion pressure of foams is set forth in the TEST METHODS section hereafter.

The expansion pressure for polymeric foams of the present invention is about 30 kiloPascals (kPa) or less and typically from about 7 to about 20 kPa, i.e. the expansion pressure is within a relatively narrow range. This means the elastic recovery tendency of typical polymeric foams according to the present invention is relatively constant. Accordingly, the capillary pressures necessary to provide collapsed, unexpanded polymeric foam materials according to the present invention also typically fall within a constant range.

It might be theoretically possible to measure directly the capillary pressures developed within the foam structure of collapsed polymeric foams according to the present invention. For example, if modeled simply as a hollow cylinder, the capillary pressure (P) can be defined by the Laplace equation:

$$P = \frac{2\gamma \cos(\theta)}{r_c}$$

where $\gamma$ is the surface tension of the fluid, $\Theta$ is the contact angle, and $r_c$ is the radius of a capillary tube. However, because of various complicating factors, including the difficulty in assigning a value to $r_c$ for the polymeric foam, the capillary pressures developed within the foam structures of the present invention are not measured directly. Instead, the capillary pressures developed within the foam structure are more easily estimated by rewriting the above Laplace equation in the following, more general form, that is applicable to any porous structure (e.g., foams):

$$P = \frac{S_c p}{\phi} \gamma \cos\theta$$

wherein $S_c$ is the capillary suction specific surface area of the foam structure, p is the foam density, $\phi$ is the porosity of the foam, and $\gamma \cos \Theta$ is the adhesion tension (AT) between the fluid and the foam structure. Assuming the value for $\phi$ is close to 1 (typically the case when the foam structure is in its expanded state), the capillary pressures developed within the foam structure are essentially a function of: (A) the capillary suction specific surface area; (B) the foam density; and (C) the adhesion tension between the fluid and the foam structure.

For a constant adhesion tension value, it has been found that the specific surface area per foam volume is particularly useful for empirically defining foam structures of the present invention that will remain in a collapsed state. As used herein, "specific surface area per foam volume" refers to the capillary suction specific surface area of the foam structure times the foam density, i.e. the value $S_c p$ in the above general equation. This specific surface area per foam volume value is characterized as "empirical" in that it is derived from (a) the capillary suction specific surface area which is measured during wetting of the dried foam structure, and (b) the density of the expanded foam structure after wetting to saturation, rather than by direct measurement of the dried, collapsed foam structure. Even so, it has been found that certain minimum specific surface area per foam volume values are correlatable to the ability of the foam structure to remain in a collapsed state. Polymeric foams according to the present invention having specific surface area per foam volume values of at least about 0.025 m²/cc, preferably at least about 0.05 m²/cc, most preferably at least about 0.07 m²/cc have been found empirically to remain in a collapsed state.

Capillary suction specific surface area, foam density and the surface tension component of adhesion tension of the fluid, as well as other factors relevant to the capillary pressure and/or expansion pressure of the polymeric foam, are discussed more fully hereafter:

A) Capillary Suction Specific Surface Area

Capillary suction specific surface area is, in general, a measure of the test-liquid-accessible surface area of the polymeric network forming a particular foam per unit mass of the bulk foam material (polymer structural material plus solid residual material). Capillary suction specific surface area is determined both by the dimensions of the cellular units in the foam and by the density of the polymer. Capillary suction specific surface area is thus a way of quantifying the total amount of solid surface provided by the foam network to the extent that such a surface participates in absorbency.

The capillary suction specific surface area of an open-celled foam structure such as the polymeric foams herein is a key feature that influences the capillarity (or capillary suction) exhibited by the foam. Foams of relatively high capillary suction specific surface area and low density provide the very desirable combination of high capacity and high capillarity. High specific surface area is also a consequence of the fineness of the struts making up the foam structure. It has been found that foam capillarity must be controlled and selected so that the foam materials herein have sufficient capillarity to provide acceptable fluid retention and wicking rate of the fluid to occur within the foam structure. Adjustment of capillary suction specific surface area, as well as control of the hydrophilicity of the foam polymer surfaces, is thus the means for providing the requisite degree of capillarity for the absorbent foams of this invention.

The capillary suction specific surface area is particularly relevant to whether adequate capillary pressures are developed within the foam structure to keep it in a collapsed state until wetted with aqueous body fluids. Using the general form of the Laplace equation above, the capillary pressure developed within the foam structure is proportional to the capillary suction specific surface area. Assuming other factors such as the foam density and adhesion tension of the fluid are constant, this means that, as the capillary suction specific surface area is increased (or decreased) the capillary pressure within the foam structure also increases (or decreases) proportionately.

The capillary suction specific surface area of the foam herein can be influenced and controlled by adjusting various compositional and processing parameters that affect foam formation. For HIPE emulsion-based foams, compositional parameters include the water-to-oil ratio of the HIPE emulsion, and the type and amounts of monomers, emulsifiers, and electrolytes utilized in the HIPE emulsion. Process parameters affecting capillary suction specific surface area include mixing energy and temperature.

For purposes of this invention, capillary suction specific surface area is determined by measuring the amount of capillary uptake of a low surface tension liquid (e.g., ethanol) which occurs within a foam sample of a known mass and dimensions. A detailed description of such a procedure for determining foam specific surface area via the capillary suction method is set forth in the TEST METHODS section hereafter. Any reasonable alternative method for determining capillary suction specific surface area can also be utilized.

The collapsed open-celled, absorbent polymeric foams which are useful in the present invention are those that have a capillary suction specific surface area of at least about 0.3 m²/g. Typically, the capillary suction specific surface area is in the range from about 0.7 to about 8 m²/g, preferably from about 1 to about 7 m²/g, most preferably from about 1.5 to about 6 m²/g. For pore volumes to be defined hereafter, hydrophilic foams having such capillary suction specific surface area values will generally possess an especially desirable balance of absorbent capacity, fluid-retaining and fluid-wicking or distribution characteristics for aqueous body liquids such as urine. In addition, foams having such capillary suction specific surface areas can develop a sufficient capillary pressure to keep the foam in a collapsed, unexpanded state until wetted with such aqueous body fluids.

B) Foam Density

Foam density in grams of foam per cubic centimeter of foam volume in air is specified herein on a dry basis. Thus the amount of absorbed aqueous liquid, e.g., residual salts and liquid left in the Foam, for example, after HIPE emulsion polymerization, washing and/or hydrophilization, is disregarded in calculating and expressing foam density. Foam density as specified herein does include, however, other residual materials such as emulsifiers present in the polymerized foam. Such residual materials can, in fact, contribute significant mass to the foam material.

The density of the foam materials herein, like capillary suction specific surface area, can influence a number of performance and mechanical characteristics of the absorbent foams herein. These include the absorbent capacity for aqueous body fluids, the extent and rate of fluid distribution within the foam and the foam flexibility and compression deflection characteristics. Importantly also, the density of the foam absorbent structures herein can determine the cost effectiveness of such structures. Most importantly, foam density can partially determine what capillary pressures are sufficient to keep the foam in a collapsed, unexpanded state over substantial periods of time until wetted with aqueous body fluids.

Any suitable gravimetric procedure which will provide a determination of mass of solid foam material per unit volume of foam structure can be used to measure foam density. For example, an ASTM gravimetric procedure described more fully in the TEST METHODS section hereafter is one method which can be employed for density determination. For those situations where the foam sample preparation procedures (drying, aging, preflexing, etc.,) can inadvertently alter the density measurements obtained, then alternate density determination tests can also be utilized. Such alternative methods, for example, can include gravimetric density measurements using a test liquid absorbed within the foam material. This type of density determination method can be useful for characterizing very low density foams such as the foams herein wherein the dry density approximates the inverse of the pore volume of the foam. [See Chatterjee, "Absorbency," *Textile Science and Technology*, Vol. 7, 1985, p. 41.] As with capillary suction specific surface area, the ranges for foam density set forth hereafter are intended to be inclusive, i.e., they are intended to encompass density values that can be determined by any reasonable experimental test method.

The collapsed absorbent polymeric foams of the present invention have dry basis density values in the range of from about 0.05 to about 0.4 g/cm$^3$, preferably from about 0.07 to about 0.25 g/cm$^3$, and most preferably from about 0.1 to about 0.2 g/cm$^3$. The density of the foam materials can be adjusted to within the foregoing ranges by controlling, in particular, the water-to-oil ratio of the HIPE emulsion.

C) Surface Tension of Fluid

As previously noted, the collapsed polymeric foam materials of the present invention have a certain level of residual water. In the absence of other surface tension modifying agents, pure water has a surface tension of about 73 dynes/cm at 22° C. However, this residual water typically contains other materials that will either increase or decrease its surface tension. These materials can be present in the water phase of the HIPE emulsion from which the polymeric foam materials of the present invention are typically made. These materials can also be included in the residual water as a result of post-polymerization steps, e.g., to hydrophilize the foam surface.

One such material present in the residual water of the collapsed polymeric foam is a toxicologically acceptable hydroscopic, hydratable salt, preferably calcium chloride. In addition to keeping the residual water in the foam structure from evaporating, these hydratable salts can also increase the surface tension of the water. For example, inclusion of 1% by weight calcium chloride increases the surface tension of water to about 75 dynes/cm at 22° C. These hydratable salts are present in the foam-structure in an amount of at least about 0.1% by weight of the foam, and typically in the range of from about 0.1 to about 8%, preferably from about 3 to about 6%, by weight of the foam.

Another material that is present in the collapsed polymeric foam materials are certain oil-soluble emulsifiers. Representative oil-soluble emulsifiers that can be present in the foam structures of the present invention include sorbitan laurate (e.g., SPAN® 20), mixtures of sorbitan laurate with sorbitan palmitate (e.g., SPAN® 40), mixtures of sorbitan laurate with certain polyglycerol fatty acid esters to be described hereafter, and sorbitan oleate (e.g., SPAN® 80). These emulsifiers are typically incorporated for the purpose of rendering the surface of the foam structure hydrophilic. However, the more water-soluble components in these emulsifiers can also be dissolved in the residual water present in the foam structure and can affect its surface tension, typically by decreasing it. These oil soluble emulsifiers are present in the foam structure in an amount of at least about 0.5% by weight of the foam and typically in the range of from about 0.5 to about 20%, preferably from about 5 to about 12%, by weight of the foam.

D) Cell Size

An alternative feature which can be useful in defining preferred collapsed polymeric foam materials of this invention is cell size. Foam cells, and especially cells which are formed by polymerizing a monomer-containing oil phase that surrounds relatively monomer-free water-phase droplets, will frequently be substantially spherical in shape. The size or "diameter" of such substantially spherical cells is thus yet another commonly utilized parameter for characterizing foams in general as well as for characterizing certain preferred absorbent foam structures of the present invention. Since cells in a given sample of polymeric foam will not necessarily be of approximately the same size, an average cell size, i.e., average cell diameter, will often be specified.

As with foam density, and capillary suction specific surface area, cell size is a foam parameter which can also impact on a number of important mechanical and performance features of the absorbent foam material of this invention. Since cell size contributes to capillary suction specific surface area which, together with foam hydrophilicity, determine the capillarity of the foam, cell size is a foam structure parameter that can directly affect the internal fluid wicking properties of the foam absorbents herein, as well as the capillary pressure that is developed within the foam structure.

A number of techniques are available for determining the average cell size of foams. These techniques include mercury porosimetry methods which are well known in the art. The most useful technique, however, for determining cell size in foams involves a simple measurement based on the scanning electron photomicrograph of a foam sample. FIG. 2, for example, shows a typical HIPE foam structure according to the present invention in its expanded state. Superimposed on the photomicrograph is a scale representing a dimension of 20 microns. Such a scale can be used to determine average cell size via an image analysis procedure. Image analysis of photomicrographs of foam samples is, in fact, a commonly employed analytical tool which can be used to determine average cell size of the foam structures herein. Such a technique is described in greater detail in U.S. Pat. No. 4,788,225 (Edwards et al), issued Nov. 29, 1988, which is incorporated by reference.

The cell size measurements given herein are based on the number average cell size of the foam in its expanded state e.g., as shown in FIG. 2. The foams useful as absorbents for aqueous body fluids in accordance with the present invention will preferably have a number average cell size of about 50 microns or less and typically in the range of from about 5 to about 50 microns. More preferably, the number average cell size will be in the range from about 5 to about 40 microns, most preferably, from about 5 to about 35 microns.

The size or diameter of the cells in the foams herein can be influenced and controlled by variation of the same type of foam compositional and processing features that influence capillary suction specific surface area and foam density, For the preferred HIPE-based foams, these include primarily those factors which determine the size of the water-phase droplets in the HIPE emulsion precursor of the polymeric foam structures herein. Thus, cell size can be varied by adjusting the energy input during mixing and the type and amount of emulsifier used to form the HIPE emulsion.

E) Plasticization Effects

The oil-soluble emulsifiers present in the collapsed foam structure can affect the polymer modulus itself, e.g., as a plasticizer. These plasticizer effects can either be the result of the incorporation of the emulsifier during the formation of the HIPE emulsion, or else can be due to incorporation as a result of post-polymerization hydrophilization treatments. Plasticization by the emulsifiers usually tends to decrease the polymer modulus and thus lowers the expansion pressure of the foam structure. This means that the capillary pressure required for stable collapsed foam structures can be somewhat reduced. However, plasticization to too great an extent can also be undesirable. For example, the polymeric foam structure can be plasticized to the extent that the foam is weakened and does not have the resistance to Compression deflection characteristics specified hereafter.

II. Expanded State

A) Density Upon Saturation With Synthetic Urine

A particularly important property of the absorbent foams of the present invention in their expanded state is their density upon saturation with aqueous body fluids, relative to the dry basis density of the absorbent foam in its collapsed state. The density of the expanded foam when saturated with aqueous body fluids, relative to its dry basis density in its collapsed (compressed) state, provides a measure of the relative thickness of the foam in its expanded state. This provides a particularly relevant measure of how thin the foam is when expanded and when saturated with aqueous body fluids.

For the purposes of the present invention, the density of the absorbent foams in their expanded state is measured when it is saturated at 88° F. (31.1° C.) to its free absorbent capacity with synthetic urine having a surface tension of 65±5 dynes/cm. The density of the foam in its expanded state when saturated with the synthetic urine can be measured by a procedure described more fully hereafter in the Test Methods section. The density of the foam measured in its expanded, saturated state, is then related, as a percentage, to the dry basis density of the foam in its collapsed state. For the purposes of the present invention, the density of the foam in its expanded state upon saturation to its free absorbent capacity with synthetic urine can be in the range of from about 10 to about 50% of its dry basis density in its collapsed state, and is preferably in the range of from about 10 to about 30%, most preferably from about 15 to about 25%.

B) Pore Volume

Pore volume is a measure of the volume of the openings or cells in a porous foam structure per unit mass of solid material (polymer structure plus any residual solids) which forms the foam structure. Pore volume can be important in influencing a number of performance and mechanical features of the absorbent foams herein, especially in their expanded state. Such performance and mechanical features include absorbent capacity of the foams for aqueous body fluids, foam flexibility and foam compression deflection characteristics.

Pore volume can be determined by any suitable experimental method which will give an accurate indication of the actual pore volume of the structure. Such experimental methods will generally involve the measurement of the volume and/or mass of a test liquid which can be introduced into the foam structure and which therefore is representative of the volume occupied by the open cells of the foam. For this reason the pore volume parameter of the foams herein can also be referred to as "available pore volume."

One conventional way for determining available pore volume experimentally involves the introduction of a low surface tension, nonpolymer-swelling liquid such as 2-propanol into the foam structure. A procedure for determining available pore volume using 2-propanol is set forth hereafter in the TEST METHODS section. It should be understood, however, that alternative test liquids and procedures can also be used to determine available pore volume.

The pore volume of the absorbent foams useful herein can be influenced and controlled by adjusting a number of foam compositional and processing features. For example, with the preferred HIPE emulsion-based foams herein, these pore volume influencing features can include the water-to-oil ratio of the HIPE emulsion, type and amount of water phase electrolyte used, type and amount of oil phase emulsifier used, post-polymerization steps to effect washing and/or densification of the foam and degree of recovery of the polymerized foam structure after such steps.

The foam materials of the present invention will generally have a pore volume of from about 12 to about 100 mL/g, more preferably from about 20 to about 70 mL/g, and most preferably from about 25 to about 50 mL/g. Such ranges for pore volume are intended to be an "inclusive" definition of theoretical pore volume for the foams encompassed by this invention. Thus if any experimental method which can reasonably be expected to give measurements approximating theoretical pore volume provides values within the foregoing ranges, then the foam materials tested by any such method are within the scope of this invention.

C) Resistance to Compression Deflection

An important mechanical feature of the polymeric foams of this invention is the strength of the absorbent foam, in its expanded state, as determined by its resistance to compression deflection. The resistance to compression deflection exhibited by the foams herein is a function of the polymer elastic modulus and the density of the foam network. The polymeric elastic modulus is, in turn, determined by a) the polymeric composition; b) the extent to which the polymeric foam is plasticized by residual material, e.g., emulsifiers, left in the foam structure after processing; and c) the conditions under which the foam was polymerized.

To be useful as absorbent structures in absorbent articles such as diapers, the absorbent foam materials of the present invention must be suitably resistant to deformation or compression by forces encountered when such absorbent materials are engaged in the absorption and retention of fluids. Foams which do not possess sufficient foam strength in terms of resistance to compression deflection may be able to acquire and store acceptable amounts of body fluid under no-load conditions but will too easily give up such fluid under the compressive stress caused by the motion and activity of the wearer of the absorbent articles which contain the foam.

The resistance to compression deflection exhibited by the polymeric foams of the present invention can be quantified by determining the amount of strain produced in a sample of saturated foam material held under a certain confining pressure for a specified period of time. For the purposes of the present invention such measurements can be made on a foam sample of standard size (cylinders which are 0.25 cm thick and have a cross-sectional circular area of 6.5 cm$^2$). Such samples are saturated with synthetic urine having a surface tension of 65±5 dynes/cm and are thereafter subjected to a confining pressure of 5.1 kPa for a period of 15 minutes at a temperature of 88° F. (31.1° C.). The amount of strain produced in such testing is reported as a percentage of the saturated and fully expanded sample thickness that the compressed thickness of the sample represents. The method for carrying out this particular type of test for quantifying resistance to compression deflection is set forth hereafter in greater detail in the TEST METHODS section.

The absorbent foams useful herein are those which exhibit a resistance to compression deflection such that a confining pressure of 5.1 kPa produces a strain of typically from about 2 to about 80% compression of the foam structure when it has been saturated to its free absorbent capacity with synthetic urine having a surface tension of 65±5 dynes/cm. Preferably the strain produced under such conditions will be in the range from about 5 to about 40%, most preferably from about 5 to about 25%. For the preferred HIPE foams of this invention, resistance to compression deflection can be adjusted to strain values within the foregoing ranges by appropriate selection of monomer, comonomer and crosslinker types and concentrations in combination with the selection of appropriate emulsion formation and emulsion polymerization conditions and techniques. Thus, such preferred foams can be formed from materials with elastic modulii large enough to provide adequate resistance to compression deflection even though such foams are low density and have very fine struts.

D) Recovery From Compression Deflection

Recovery from compression deflection relates to the tendency or propensity of a piece of foam material to return to its original dimensions after being deformed or compressed under forces encountered in manufacture, storage or use. For purposes of the present invention, recovery from compression deflection of the preferred absorbent foams herein are determined on foams which are in their expanded state, and contain absorbed body fluid. Accordingly, recovery from compression deflection is measured on expanded foams which are saturated with synthetic urine.

A suitable procedure for determining recovery from compression deflection is set forth in the TEST METHODS section hereafter. Such a procedure in general involves compression and release of a standard size foam sample which has been saturated to its free absorbent capacity with synthetic urine. Samples are maintained under 50% compression for a set period of time and then are released from compression. The extent to which the sample recovers its thickness, in the presence of available free fluid, in the one-minute period after the release of compressive force is taken as a measure of the recovery from compression deflection (resilience) propensity of the sample.

Preferred absorbent foams of the present invention will generally exhibit a recovery of at least 75% of the expanded caliper when wet after one minute. More preferably, such preferred foam materials will have a recovery from compression deflection at least 80% when wet.

III. Collapsed or Expanded State

A) Flexibility

The absorbent foams of the present invention should be sufficiently flexible so that they can be utilized in absorbent products that will conform to the body shape of the wearer. Characterization of the absorbent foams herein as flexible, therefore, means that these foams can be deformed or bent to the extent necessary for use in such absorbent articles without significant damage to their structural integrity or significant loss of their absorbent properties.

Preferred absorbent foams of the present invention should also be sufficiently flexible to withstand compressive or deforming forces which are encountered during preparation, processing, packaging, shipping and storing of absorbent articles containing such foam materials. Disposable diapers, for example, are generally packaged and marketed in a folded condition wherein the diaper core is folded in both the longitudinal and transverse directions. Disposable diapers are also generally marketed in the form of stacks of folded diapers, which stacks are contained and compressed by their surrounding packaging. Accordingly, the compressive and deforming forces to which the foam absorbents herein can be subjected during processing and marketing can be even greater than those which are applied to the foam materials in use.

Given the nature of treatment which the absorbent foams herein can encounter, preferred absorbent foam materials of this invention will possess flexibility characteristics which can be quantified by referencing their ability to withstand bending without undergoing significant damage to their structural integrity. Described in the VEST METHODS section hereafter is a procedure for measuring the flexibility of the absorbent foams herein by determining whether and how many times a foam sample of a given specified size can be bent around a cylindrical mandrel at a specified rate without breaking. The preferred foams of this invention are those which are flexible enough so that, at their point of use as an absorbent for body fluids, the saturated foam material at 88° F. (31.1° C.) can be subjected to this bending test without breaking, i.e., exhibit a bending value of at least one cycle. More preferably, preferred foams can be bent at least 3 times without breaking when subjected to such a test procedure.

B) Foam Integrity and Softness

While not absolutely essential for the realization of operable or useful absorbent structures, the absorbent foams of this invention will preferably possess the additional mechanical attributes of structural integrity in use and softness (lack of irritation) to the touch. For example, foam materials that will be employed in absorbent articles such as infant diapers will frequently be subjected to both dynamic and static forces which arise when the wearer walks, runs, crawls or jumps. Such forces not only tend to compress the absorbent foams and expel fluid therefrom, but such forces also tend to rip or tear or otherwise fragment the foam structure. Obviously, it would be advantageous for foam structures which are to be used in this manner to have sufficient structural integrity to minimize the incidence of foam tearing or fragmenting in use.

The absorbent foams of this invention can also be used in absorbent articles, as described more fully hereafter, in configurations wherein the foam material surface can come in close proximity to or even in actual contact with the wearer's skin. Accordingly, it would be very desirable for the surface of the absorbent foams herein to be acceptably soft and non-irritating to the touch.

IV. Fluid Handling and Absorbency Characteristics

Absorbent foams having suitable polymeric compositions, and the structural characteristics and mechanical features as hereinbefore described, will in general exhibit especially desirable and useful body fluid handling and absorbency characteristics. Such fluid handling and absorbency characteristics are in turn the attributes of the preferred foam materials herein which render such foams especially suitable for use as absorbent structures in absorbent articles designed to acquire and hold aqueous body fluids.

The fluid handling and absorbency characteristics which are most relevant to the realization of suitable absorbent foams are: A) the free absorbent capacity of the foam; B) the rate of vertical wicking of fluid through the foam structure; C) the absorbent capacity of the foam at specific reference wicking heights; and D) the ability of the absorbent foam structures to drain (partition) fluid from competing absorbent structures with which the foam can be in contact. Each of these characteristics is described in greater detail as follows:

A) Free Absorbent Capacity

Free absorbent capacity is the total amount of test fluid (synthetic urine) which a given foam sample will absorb into its cellular structure per unit mass of solid material in the sample. Such free absorbent capacity measurements are for purposes herein calculated at equilibrium, i.e., after the foam sample has been allowed to acquire and/or hold all of the fluid it can over whatever time period is needed to form a completely saturated foam sample with the test liquid. The foam materials which are especially useful as absorbent structures in absorbent articles such as diapers will at least meet a minimum free absorbent capacity.

Using the procedure described in greater detail hereafter in the TEST METHODS section, free absorbent capacity can both be determined for any given foam sample by a gravimetric analysis technique. In such a technique, a foam sample of specified known size and weight is placed in a dish of test fluid (synthetic urine) and is allowed to absorb the test fluid to equilibrium. After removal of the saturated sample from the fluid, the amount of fluid held per gram of foam, i.e., the measured free capacity, is then calculated. To be especially useful in absorbent articles for absorbing urine, the absorbent foams of the present invention should have a free capacity of at least about 12, and preferably at least about 20, mL of synthetic urine per gram of dry foam material.

B) Vertical Wicking Performance

Yet another fluid handling attribute of the absorbent foams useful herein relates to their ability to quickly move or "wick" acceptable amounts of body fluids through their foam structures. Vertical wicking, i.e., fluid wicking in a direction opposite from gravitational force, is an especially desirable performance attribute for the absorbent foam materials herein. This is because such materials will frequently be utilized in absorbent articles in a manner that fluid to be absorbed must be moved within the article from a relatively lower position to a relatively higher position within the absorbent core of the article.

Vertical wicking performance is related to the magnitude of the capillary suction driving force which moves liquid through the foam and holds it in the foam structure. Foam characterizing parameters which relate to vertical wicking propensity thus provide an indication as to how well preferred foams herein will perform as absorbent structures in absorbent articles. For the foam absorbents of the present invention, fluid wicking propensity can be quantified by referencing both a vertical wicking rate test and a vertical wicking absorbent capacity test.

1) Vertical Wicking Rate

The vertical wicking rate test measures the time taken for a colored test liquid (e.g., synthetic urine) from a reservoir to wick a vertical distance of 5 cm through a test strip of foam of specified size when the test is performed at 37° C. Such a vertical wicking rate test is described in greater detail hereafter in the TEST METHODS section. To be especially useful in absorbent articles for absorbing urine, the foam absorbents of the present invention will preferably have a 5 cm vertical wicking rate of no more than about 30 minutes when wicking synthetic urine (65±5 dynes/cm). More preferably, the preferred foam absorbents of the present invention will have a 5 cm vertical wicking rate of no more than about 5 minutes when wicking synthetic urine.

2) Vertical Wicking Absorbent Capacity

The vertical wicking absorbent capacity test is carried out in conjunction with the vertical wicking rate test. Vertical wicking absorbent capacity measures the amount of test fluid per gram of absorbent foam that is wicked to each one inch (2.54 cm) vertical section of the same standard size foam sample used in the vertical wicking rate test. Such a determination is generally made after the sample has been allowed to vertically wick test fluid to equilibrium (e.g., after about 18 hours). Like the vertical wicking rate test, the vertical wicking absorbent capacity test is described in greater detail hereafter in the TEST METHODS section.

To be especially useful in absorbent articles for absorbing urine, the preferred absorbent foams of the present invention will generally have a vertical wicking absorbent capacity such that, at 11.4 cm (4.5 inches) of vertical wicking height, the foam test strip wicks to at least about 50%, most preferably at about 75%, of its free absorbent capacity.

C) Partitioning

The absorbent foam structures herein will frequently be utilized in absorbent articles along with other types of absorbent structures which can also participate in acquiring, distributing and/or storing discharged body fluids. In those contexts wherein the foam structures herein are to serve primarily as a fluid storage/redistribution component in absorbent articles, it is desirable for such foams to have a propensity for pulling body fluids into the foam structure from other absorbent components which also are absorbing such fluids. Such a propensity to drain fluid from other absorbent article components is known in the art as "partitioning." The concept of partitioning and certain procedures for determining partitioning performance are described, for example, in U.S. Pat. No. 4,610,678 (Weisman et al), issued Sep. 9, 1986. When tested for partitioning performance using procedures similar to those disclosed in U.S. Pat. No. 4,610,678, the absorbent foam structures of this invention exhibit especially desirable fluid partitioning characteristics.

V. Preparation of Collapsed Polymeric Foam Materials

As previously noted, collapsed polymeric foam materials according to the present invention can be prepared by polymerization of certain water-in-oil emulsions having a relatively high ratio of water phase to oil phase. Emulsions of this type which have these relatively high water to oil phase ratios are commonly known in the art as high internal phase emulsions ("HIPEs" or "HIPE" emulsions). The polymeric foam materials which result from the polymerization of such emulsions are referred to herein as "HIPE foams."

The chemical nature, makeup and morphology of the polymer material which forms the HIPE foam structures herein is determined by both the type and concentration of the monomers. comonomers and crosslinkers utilized in the HIPE emulsion and by the emulsion formation and polymerization conditions employed. No matter what the particular monomeric makeup, molecular weight or morphology of the polymeric material might be, the resulting polymeric foams will generally be viscoelastic in character, i.e. the foam structures will possess both viscous, i.e. fluid-like, properties and elastic, i.e. spring-like, properties. It is also important that the polymeric material which forms the cellular foam structure have physical, rheological, and morphological attributes which, under conditions of use, impart suitable flexibility, resistance to compression deflection, and dimensional stability to the absorbent foam material.

The relative amounts of the water and oil phases used to form the HIPE emulsions are, among many other parameters, important in determining the structural, mechanical and performance properties of the resulting polymeric foams. In particular, the ratio of water to oil in the foam-forming emulsion can influence the foam density, cell size, and capillary suction specific surface area of the foam and dimensions of the struts which form the foam. The emulsions used to prepare the HIPE foams of this invention will generally have water-to-oil phase ratios ranging from about 12:1 to about 100:1, more preferably from about 20:1 to about 70:1, most preferably from about 25:1 to about 50:1.

A. Oil Phase Components

The continuous oil phase of the HIPE emulsion comprises monomers that are polymerized to form the solid foam structure. This monomer component includes a "glassy" monomer, a "rubbery" comonomer and a cross-linking agent. Selection of particular types and amounts of monofunctional monomer(s) and comonomer(s) and polyfunctional cross-linking agent(s) can be important to the realization of absorbent HIPE foams having the desired combination of structure, mechanical, and fluid handling properties which render such materials suitable for use in the invention herein.

The monomer component utilized in the oil phase of the HIPE emulsions comprises one or more monofunctional monomers that tend to impart glass-like properties to the resulting polymeric foam structure. Such monomers are referred to as "glassy" monomers, and are, for purposes of this invention, defined as monomeric materials which would produce high molecular weight (greater than 6000) homopolymers having a glass transition temperature, $T_g$, above about 40° C. These monofunctional glassy monomer types include methacrylate-based monomers (e.g., methyl methacrylate) and styrene-based monomers (e.g., styrene). The preferred monofunctional glassy monomer type is a styrene-based monomer with styrene itself being the most preferred monomer of this kind. Substituted, e.g., monosubstituted, styrene such as p-methylstyrene can also be employed. The monofunctional glassy monomer will normally comprise from about 5 to about 40%, more preferably from about 10 to about 30%, more preferably from about 15 to about 25%, most preferably about 20%, by weight of the monomer component.

The monomer component also comprises one or more monofunctional comonomers which tend to impart rubber-like properties to the resulting polymeric foam structure. Such comonomers are referred to as "rubbery" comonomers and are, for purposes of this invention, defined as monomeric materials which would produce high molecular weight (greater than 10,000) homopolymers having a glass transition temperature, $T_g$, of about 40° C. or lower. Monofunctional rubbery comonomers of this type include, for example, the $C_4$–$C_{12}$ alkylacrylates, the $C_6$–$C_{14}$ alkylmethacrylates, and combinations of such comonomers. Of these comonomers, n-butylacrylate and 2-ethylhexylacrylate are the most preferred. The monofunctional rubbery comonomer will generally comprise from about 30 to about 80%, more preferably from about 50 to about 70%, most preferably from about 55 to about 65%, by weight of the monomer component.

Since the polymer chains formed from the glassy monomer(s) and the rubbery comonomer(s) are to be cross-linked, the monomer component also contains a polyfunctional cross-linking agent. As with the monofunctional monomers and comonomers, selection of a particular type and amount of cross-linking agent is very important to the eventual realization of preferred polymeric foams having the desired combination of structural, mechanical, and fluid-handling properties.

Depending upon the type and amounts of monofunctional monomers and comonomers utilized, and depending further upon the desired characteristics of the resulting polymeric foams, the polyfunctional cross-linking agent can be selected from a wide variety of polyfunctional, preferably difunctional, monomers. Thus, the cross-linking agent can be a divinyl aromatic material such as divinylbenzene, divinyltolulene or diallylphthalate. Alternatively, divinyl aliphatic crosslinkers such as any of the diacrylic or dimethylacrylic acid esters of polyols, such as 1,6-hexanediol and its homologues, can be utilized. The cross-linking agent found to be suitable for preparing the preferred HIPE emulsions herein is divinylbenzene. The cross-linking agent of whatever type will generally be employed in the oil phase of the foam-forming emulsions herein in an amount of from about 10 to about 40%, more preferably from about 15 to about 25%, most preferably about 20%, by weight of the monomer component.

The major portion of the oil phase of the HIPE emulsions will comprise the aforementioned monomers, comonomers and crosslinking agents. It is essential that these monomers, comonomers and cross-linking agents be substantially water-insoluble so that they are primarily soluble in the oil phase and not the water phase. Use of such substantially water-insoluble monomers insures that HIPE emulsions of appropriate characteristics and stability will be realized.

It is, of course, highly preferred that the monomers, comonomers and cross-linking agents used herein be of the type such that the resulting polymeric foam is suitably non-toxic and appropriately chemically stable. These monomers, comonomers and cross-linking agents should preferably have little or no toxicity if present at very low residual concentrations during post-polymerization foam processing and/or use.

Another essential component of the oil phase is an emulsifier which permits the formation of stable HIPE emulsions. Such emulsifiers are those which are soluble in the oil phase used to form the emulsion. Emulsifiers utilized are typically nonionic and include the sorbitan fatty acid esters, the polyglycerol fatty acid esters, and combinations thereof. Preferred emulsifiers include sorbitan laurate (e.g., SPAN® 20), sorbitan oleate (e.g., SPAN® 80), combinations of sorbitan laurate and sorbitan palmitate (e.g., SPAN® 40) in a weight ratio of from about 1:1 to about 3:1, and especially combinations of sorbitan laurate with certain polyglycerol fatty acid esters to be described hereafter.

The oil phase used to form the HIPE emulsions will generally comprise from about 67 to about 98% by weight monomer component and from about 2 to about 33% by weight emulsifier component. Preferably, the oil phase will comprise from about 80 to about 95% by weight monomer component and from about 5 to about 20% by weight emulsifier component.

In addition to the monomer and emulsifier components, the oil phase can contain other optional components. One such optional oil phase component is an oil soluble polymerization initiator of the general type hereafter described. Another possible optional component of the oil phase is a substantially water insoluble solvent for the monomer and emulsifier components. A solvent of this type must, of course, not be capable of dissolving the resulting polymeric foam. Use of such a solvent is not preferred, but if such a solvent is employed, it will generally comprise no more than about 10% by weight of the oil phase.

B. Water Phase Components

The discontinuous internal phase of the HIPE emulsions is the water phase which will generally be an aqueous solution containing one or more dissolved components. One essential dissolved component of the water phase is a water-soluble electrolyte. The dissolved electrolyte in the water phase of the HIPE emulsion serves to minimize the tendency of monomers and crosslinkers which are primarily oil soluble to also dissolve in the water phase. This, in turn, is believed to minimize the extent to which, during polymerization of the emulsion, polymeric material fills the cell windows at the oil/water interfaces formed by the water phase droplets. Thus, the presence of electrolyte and the resulting ionic strength of the water phase is believed to determine whether and to what degree the resulting preferred polymeric foams can be open-celled.

Any electrolyte which provides ionic species to impart ionic strength to the water phase can be used. Preferred electrolytes are mono-, di-, or tri-valent inorganic salts such as the water-soluble halides, e.g., chlorides, nitrates and sulfates of alkali metals and alkaline earth metals. Examples include sodium chloride, calcium chloride, sodium sulfate and magnesium sulfate. Calcium chloride is the most preferred for use in the present invention. Generally the electrolyte will be utilized in the water phase of the HIPE emulsions in a concentration in the range of from about 0.2 to about 20% by weight of the water phase. More preferably, the electrolyte will comprise from about 1 to about 10% by weight of the water phase.

The HIPE emulsions will also typically contain a polymerization initiator. Such an initiator component is generally added to the water phase of the HIPE emulsions and can be any conventional water-soluble free radical initiator. Materials of this type include peroxygen compounds such as sodium, potassium and ammonium persulfates, hydrogen peroxide, sodium peracetate, sodium percarbonate and the like. Conventional redox initiator systems can also be utilized. Such systems are formed by combining the foregoing peroxygen compounds with reducing agents such as sodium bisulfite, L-ascorbic acid or ferrous salts.

The initiator material can comprise up to about 5 mole percent based on the total moles of polymerizable monomers present in the oil phase. More preferably, the initiator comprises from about 0.001 to 0.5 mole percent based on the total moles of polymerizable monomers in the oil phase. When used in the water-phase, such initiator concentrations can be realized by adding initiator to the water phase to the extent of from about 0.02% to about 0.4%, more preferably from about 0.1% to about 0.2%, by weight of the water phase.

C. Hydrophilizing Agents and Hydratable Salts

The cross-linked polymer material that forms the collapsed absorbent foam structures herein will preferably be substantially free of polar functional groups on its polymeric structure. Thus, immediately after the polymerization step, the polymer material which forms the foam structure surfaces of such preferred absorbent foams will normally be relatively hydrophobic in character. Accordingly, preferred just-polymerized foams can need further treatment to render the foam structure surfaces relatively more hydrophilic so that such foams can be used as absorbents for aqueous body fluids. Hydrophilization of the foam surfaces, if necessary, can generally be accomplished by treating the polymerized HIPE foam structures with a hydrophilizing agent in a manner described more fully hereafter.

Hydrophilizing agents are any materials which will enhance the water wettability of the polymeric surfaces with which they are contacted and onto which they are deposited. Hydrophilizing agents are well known in the art, and can include surfactant materials, preferably of the nonionic type. Hydrophilizing agents will generally be employed in liquid form, and can be dissolved or dispersed in a hydrophilizing solution which is applied to the HIPE foam surfaces. In this manner, hydrophilizing agents can be adsorbed onto the polymeric surfaces of the preferred HIPE foam structures in amounts suitable for rendering such surfaces substantially hydrophilic but without altering the desired flexibility and compression deflection characteristics of the foam. In preferred foams which have been treated with hydrophilizing agents, the hydrophilizing agent is incorporated into the foam structure such that residual amounts of the agent which remain in the foam structure are in the range from about 0.5% to about 20%, preferably from about 5 to about 12%, by weight of the foam.

One type of suitable hydrophilizing agent is a non-irritating oil-soluble surfactant. Such surfactants can include all of those previously described for use as the emulsifier for the oil phase of the HIPE emulsion, such as sorbitan laurate (e.g., SPAN ® 20), and combinations of sorbitan laurate with certain polyglycerol fatty acid esters to be described hereafter. Such hydrophilizing surfactants can be incorporated into the foam during HIPE emulsion formation and polymerization or can be incorporated by treatment of the polymeric foam with a solution or suspension of the surfactant dissolved or dispersed in a suitable carrier or solvent.

Another material that needs to be incorporated into the HIPE foam structure is a hydratable, and preferably hygroscopic or deliquesent, water soluble inorganic salt. Such salts include, for example, toxicologically acceptable alkaline earth metal salts. Materials of this type and their use in conjunction with oil-soluble surfactants as the foam hydrophilizing agent is described in greater detail in the U.S. patent application Ser. No. 07/743,951, filed Aug. 12, 1991, the disclosure of which is incorporated by reference. Preferred salts of this type include the calcium halides such as calcium chloride which, as previously noted, can also be employed as the electrolyte in the water phase of the HIPE emulsions used to prepare the polymeric foams.

Hydratable inorganic salts can easily be incorporated into the polymeric foams herein by treating the foams with aqueous solutions of such salts. Solutions of hydratable inorganic salts can generally be used to treat the foams after completion of, or as part of, the process of removing the residual water phase from the just-polymerized foams. Contact of foams with such solutions is preferably used to deposit hydratable inorganic salts such as calcium chloride in residual amounts of at least about 0.1% by weight of the foam, and typically in the range of from about 0.1 to about 8%, preferably from about 3 to about 6%, by weight of the foam.

Treatment of preferred foam structures which are relatively hydrophobic as polymerized with hydrophilizing agents (with or without hydratable salts) will typically be carried out to the extent that is necessary and sufficient to impart suitable hydrophilicity to the preferred HIPE foams of the present invention. Some foams of the preferred HIPE emulsion type, however, can be suitably hydrophilic as prepared and can have incorporated therein sufficient amounts of hydratable salts, thus requiring no additional treatment with hydrophilizing agents or hydratable salts. In particular, such preferred HIPE foams can be those wherein sorbitan fatty acid esters such as sorbitan laurate (e.g., SPAN 20), or combinations of sorbitan laurate with certain polyglycerol fatty acid esters to be described hereafter, are used as emulsifiers added to the oil phase and calcium chloride is used as an electrolyte in the water phase of the HIPE emulsion. In that instance, the residual-emulsifier-containing internal polymerized foam surfaces will be suitably hydrophilic, and the residual water-phase liquid will contain or deposit sufficient amounts of calcium chloride, even after the polymeric foams have been dewatered.

D. Processing Conditions for Obtaining HIPE Foams

Foam preparation typically involves the steps of: 1) forming a stable high internal phase emulsion (HIPE); 2) polymerizing/curing this stable emulsion under conditions suitable for forming a solid polymeric foam structure; 3) washing the solid polymeric foam structure to remove the original residual water phase from the polymeric foam structure and, if necessary, treating the polymeric foam structure with a hydrophilizing agent and/or hydratable salt to deposit any needed hydrophilizing agent/hydratable salt, and 4) thereafter dewatering this polymeric foam structure (preferably including compression in the z-direction) to the extent necessary to provide a collapsed, unexpanded polymeric foam material useful as an absorbent for aqueous body fluids.

To consistently obtain relatively thin, collapsed polymeric foam materials according to the present invention, it has been found to be particularly important to carry out the emulsion formation and polymerization steps in a manner such that coalescence of the water droplets in the HIPE emulsion is reduced or minimized. HIPE emulsions are not always stable, particularly when subjected to higher temperature conditions to effect polymerization and curing. As the HIPE emulsion destabilizes, the water droplets present in it can aggregate together, and coalesce to form much large water droplets. Indeed, during polymerization and curing of the emulsion, there is essentially a race between solidification of the foam structure, and coalescence of the water droplets. An appropriate balance has to be struck such that coalescence of the water droplets is reduced, yet polymerization and curing of the foam structure can be carried out within a reasonable time. (While some coalescence can be tolerated if the remaining water droplets are very small in size, such nonuniform cell sizes in the resulting foam can adversely affect the fluid transport properties of the foam, especially its wicking rate.)

Reduction in the coalescence of water droplets in the HIPE emulsion leads to a smaller average cell size in the resulting foam structure after polymerization and curing. It is believed that this resulting smaller average cell size in the polymeric foam material is a key mechanism behind consistent formation of relatively thin, collapsed polymeric foam materials according to the present invention. (Uniformly small cell sizes in the resulting foam are also believed to lead to good absorbency, and especially fluid transport (e.g., wicking) characteristics.) The number average cell size of the polymeric foam materials is about 50 microns or less and is typically in the range from about 5 to about 50 microns, preferably from about 5 to about 40 microns, most preferably from about 5 to about 35 microns, when prepared under conditions that reduce coalescence of water droplets in the HIPE emulsion. Techniques for consistently reducing coalescence of water droplets in the HIPE emulsion will be discussed in greater detail in the following description of the emulsion formation and polymerization/curing steps for obtaining collapsed polymeric foams:

1. Formation of HIPE Emulsion

The HIPE emulsion is formed by combining the oil phase components with the water phase components in the previously specified weight ratios. The oil phase will contain the previously specified essential components such as the requisite monomers, comonomers, crosslinkers and emulsifiers. and can also contain optional components such as solvents and polymerization initiators. The water phase used will contain the previously specified electrolytes as an essential component and can also contain optional components such as water-soluble emulsifiers, and/or polymerization initiators.

The HIPE emulsion can be formed from the combined oil and water phases by subjecting these combined phases to shear agitation. Shear agitation is generally applied to the extent and for a time period necessary to form a stable emulsion from the combined oil and water phases. Such a process can be conducted in either batchwise or continuous fashion and is generally carried out under conditions suitable for forming an emulsion wherein the water phase droplets are dispersed to such an extent that the resulting polymeric foam will have the requisite pore volume and other structural characteristics. Emulsification of the oil and water phase combination will frequently involve the use of a mixing or agitation device such as a pin impeller.

One preferred method of forming HIPE emulsions which can be employed herein involves a continuous process for combining and emulsifying the requisite oil and water phases. In such a process, a liquid stream comprising the oil phase is formed and provided at a flow rate ranging from about 0.08 to about 1.5 mL/sec. Concurrently, a liquid stream comprising the water phase is also formed and provided at a flow rate ranging from about 4 to about 50 mL/sec. At flow rates within the foregoing ranges, these two streams are then combined in a suitable mixing chamber or zone in a manner such that the requisite water to oil phase weight ratios as previously specified are approached, reached and maintained.

In the mixing chamber or zone, the combined streams are generally subjected to shear agitation as provided, for example, by a pin impeller of suitable configuration and dimensions. Shear will typically be applied to the extent of from about 1000 to about 2500 sec.$^{-1}$. Residence times in the mixing chamber will frequently range from about 5 to about 30 seconds. Once formed, the stable HIPE emulsion in liquid form can be withdrawn from the mixing chamber or zone at a flow rate of from about 4 to about 52 mL/sec. This preferred method for forming HIPE emulsions via a continuous process is described in greater detail in U.S. Pat. No. 5,149,720 (DesMarais et al), issued Sep. 22, 1992, which is incorporated by reference.

In consistently reducing the coalescence of the water droplets present in the HIPE emulsion, it is particularly preferred to use certain types of emulsifier systems in the oil phase, especially if the HIPE emulsion is to be polymerized or cured at temperatures above about 50° C. These preferred emulsifier systems comprise a combination of sorbitan laurate (e.g., SPAN® 20), and certain polyglycerol fatty acid esters (PGEs) as co-emulsifiers. The weight ratio of sorbitan laurate to PGE is usually within the range of from about 10:1 to about 1:10. Preferably, this weight ratio is in the range of from about 4:1 to about 1:1.

The PGEs especially useful as co-emulsifiers with sorbitan laurate are usually prepared from polyglycerols characterized by high levels of linear (i.e.. acyclic) diglycerols, reduced levels of tri- or higher polyglycerols, and reduced levels of cyclic diglycerols. Suitable polyglycerol reactants (weight basis) usually have a linear diglycerol level of at least about 60% (typical range of from about 60 to about 90%), a tri- or higher polyglycerol level of no more than about 40% (typical range of from about 10 to about 40%), and a cyclic diglycerol level of no more than about 10% (typical range of from 0 to about 10%). Preferably, these polyglycerols have a linear diglycerol level of from about 60 to about 80%, a tri- or higher polyglycerol level of from about 20 to about 40%, and a cyclic diglycerol level of no more than about 10%. (A method for determining the polyglycerol distribution is set forth hereafter in the PGE ANALYTICAL METHODS section.)

PGEs especially useful as co-emulsifiers with sorbitan laurate are also prepared from fatty acid reactants characterized by fatty acid compositions having high levels of combined $C_{12}$ and $C_{14}$ saturated fatty acids, and reduced levels of other fatty acids. Suitable fatty acid reactants have fatty acid compositions where the combined level of $C_{12}$ and $C_{14}$ saturated fatty acids is at least about 40% (typical range of from about 40 to about 85%), the level of $C_{16}$ saturated fatty acid is no more than about 25% (typical range of from about 5 to about 25%), the combined level of $C_{18}$ or higher saturated fatty acids is no more than about 10% (typical range of from about 2 to about 10%), the combined level of $C_{10}$ or lower fatty acids is no more than about 10% (typical range of from about 0.3 to about 10%), the balance of other fatty acids being primarily $C_{18}$ monounsaturated fatty acids. Preferably, the fatty acid composition of these fatty acid reactants is at least about 65% combined $C_{12}$ and $C_{14}$ saturated fatty acids (typical range of from about 65 to about 75%), no more than about 15% $C_{16}$ saturated fatty acid (typical range of from about 10 to about 15%), no more than about 4% combined $C_{18}$ or higher saturated fatty acids (typical range of from about 2 to about 4%), and no more than about 3% $C_{10}$ or lower fatty acids (typical range of from about 0.3 to about 3%). (A method for determining the fatty acid composition is set forth hereafter in the PGE ANALYTICAL METHODS section.)

PGEs useful as co-emulsifiers with sorbitan laurate are also usually characterized as imparting a minimum oil/water interfacial tension (IFT), where the oil phase contains monomers used in the HIPE emulsion and the water phase contains calcium chloride. Suitable PGE co-emulsifiers usually impart a minimum oil/water IFT of at least about 0.06 dynes/cm, with a typical range of from about 0.06 to about 1.0 dynes/cm. Especially preferred PGEs impart a minimum oil/water IFT of at least about 0.09 dynes/cm, with a typical range of from about 0.09 to about 0.3 dynes/cm. (A method for measuring the IFT of these PGEs is set forth hereafter in the PGE ANALYTICAL METHODS section.)

PGEs useful as coemulsifiers with sorbitan monolaurate can be prepared by methods well known in the art. See, for example, U.S. Pat. No. 3,637,774 (Babayan et al), issued Jan. 25, 1972, and McIntyre, "Polyglycerol Esters," *J. Am. Oil Chem. Soc.*, Vol. 56, No. 11 (1979), pp. 835A–840A, which are incorporated by reference and which describe methods for preparing polyglycerols and converting them to PGEs. PGEs are typically prepared by esterifying polyglycerols with fatty acids. Appropriate combinations of polyglycerols can be prepared by mixing polyglycerols obtained from commercial sources or synthesized using known methods, such as those described in U.S. Pat. No. 3,637,774. Appropriate combinations of fatty acids can be prepared by mixing fatty acids and/or mixtures of fatty acids obtained from commercial sources. In making PGEs useful as co-emulsifiers, the weight ratio of polyglycerol to fatty acid is usually from about 50:50 to 70:30, preferably from about 60:40 to about 70:30.

Typical reaction conditions for preparing suitable PGE co-emulsifiers involve esterifying the polyglycerols with fatty acids in the presence of 0.1–0.2% sodium hydroxide as the esterification catalyst. The reaction is initiated at atmospheric pressure at about 210°–220° C., under mechanical agitation and nitrogen sparging. As the reaction progresses, the free fatty acids diminish and the vacuum is gradually increased to about 8 mm Hg. When the free fatty acid level decreases to less than about 0.5%, the catalyst is then neutralized with a phosphoric acid solution and the reaction mixture rapidly cooled to about 60° C. This crude reaction mixture can then be subjected to settling or other conventional purification steps (e.g., to reduce the level unreacted polyglycerol) to yield the desired PGEs.

2. Polymerization/Curing of the HIPE Emulsion

The HIPE emulsion formed will generally be collected or poured in a suitable reaction vessel, container or region to be polymerized or cured. In one embodiment herein, the reaction vessel comprises a tub constructed of polyethylene from which the eventually polymerized/cured solid foam material can be easily removed for further processing after polymerization/curing has been carried out to the extent desired. It is usually preferred that the temperature at which the HIPE emulsion is poured into the vessel be approximately the same as the polymerization/curing temperature.

Polymerization/curing conditions to which the HIPE emulsion will be subjected will vary depending upon the monomer and other makeup of the oil and water phases of the emulsion, especially the emulsifier systems used, and the type and amounts of polymerization initiators utilized. Frequently, however, polymerization/curing conditions will comprise maintenance of the HIPE emulsion at elevated temperatures above about 30° C., more preferably above about 35° C., for a time period ranging from about 4 to about 24 hours, more preferably from about 4 to about 18 hours.

In reducing coalescence of water droplets in the HIPE emulsion, it is particularly preferred to carry out the polymerization/curing at relatively lower temperatures, especially if the preferred combination of sorbitan laurate and PGE co-emulsifiers is not used in preparing the HIPE emulsion. In these situations, suitable lower polymerization/curing temperatures are in the range of from about 30° to about 50° C., preferably from about 35° to about 45° C., and most preferably about 40° C. If polymerization/curing is carried out at temperatures much above about 50° C., the thermal stress on the emulsion can cause the water droplets present to aggregate and coalesce, thus forming much larger cells in the resulting polymeric foam, especially if the preferred combination of sorbitan laurate and PGE co-emulsifiers is not used in preparing the HIPE emulsion. This can lead to polymeric foams that cannot remain in a collapsed, unexpanded state after dewatering.

A bulk solid polymeric foam is typically obtained when the HIPE emulsion is polymerized/cured in a reaction vessel, such as a tub. This bulk polymerized HIPE foam is typically cut or sliced into a sheet-like form. Sheets of polymerized HIPE foam are easier to process during subsequent treating/washing and dewatering steps, as well as to prepare the HIPE foam for use in absorbent articles. The bulk polymerized HIPE foam is typically cut/sliced to provide a cut caliper in the range of from about 0.08 to about 2.5 cm. During subsequent dewatering, this typically leads to collapsed HIPE foams having a caliper in the range of from about 0.008 to about 1.25 cm.

3. Treating/Washing HIPE Foam

The solid polymerized HIPE foam which is formed will generally be a flexible, open-cell porous structure having its cells filled with the residual water phase material used to prepare the HIPE emulsion. This residual water phase material, which generally comprises an aqueous solution of electrolyte, residual emulsifier, and polymerization initiator, should be at least partially removed from the foam structure at this point prior to further processing and use of the foam. Removal of the original water phase material will usually be carried out by compressing the foam structure to squeeze out residual liquid and/or by washing the foam structure with water or other aqueous washing solutions. Frequently several compressing and washing steps, e.g., from 2 to 4 cycles, will be utilized.

After the original water phase material has been removed from the foam structure to the extent required, the HIPE foam, if needed, can be treated, e.g., by continued washing, with an aqueous solution of a suitable hydrophilizing agent and/or hydratable salt. Hydrophilizing agents and hydratable salts which can be employed have been previously described and include sorbitan laurate (e.g., SPAN 20) and calcium chloride. As noted, treatment of the HIPE foam structure with the hydrophilizing agent/hydratable salt solution continues, if necessary, until the desired amount of hydrophilizing agent/hydratable salt has been incorporated and until the foam exhibits a desired adhesion tension value for any test liquid of choice.

4. Foam Dewatering

After the HIPE foam has been treated/washed to the extent necessary to render the eventually dried foam suitably hydrophilic, and optionally to incorporate a sufficient amount of a hydratable salt, preferably calcium chloride, the foam will generally be dewatered. Dewatering can be brought about by compressing the foam (preferably in the z-direction) to squeeze out residual water, by subjecting the foam, or the water therein, to elevated temperatures, e.g., thermal drying at temperatures from about 60° C. to about 200° C., or to microwave treatment, by vacuum dewatering or by a combination of compression and thermal drying/microwave/vacuum dewatering techniques. The dewatering step of HIPE foam processing will generally be carried out until the HIPE foam is ready for use and is as dry as practical. Frequently such compression dewatered foams will have a water (moisture) content of from about 50 to about 500%, more preferably from about 50 to about 200%, by weight on a dry weight basis. Subsequently, the compressed foams can be thermally dried (e.g., by heating) to a moisture content of from about 5 to about 40%, more preferably from about 5 to about 15%, on a dry weight basis. The resulting compressed/dried foam will be in a collapsed, unexpanded state.

VI. Absorbent Articles

The collapsed polymeric foam materials of the present invention can be used as at least a portion of the absorbent structures (e.g., absorbent cores) for various absorbent articles. By "absorbent article" herein is meant a consumer product which is capable of absorbing significant quantities of urine or other fluids (i.e., liquids), like aqueous fecal matter (runny bowel movements), discharged by an incontinent wearer or user of the article. Examples of such absorbent articles include disposable diapers, incontinence garments, catamenials such as tampons and sanitary napkins, disposable training pants, bed pads, and the like. The absorbent foam structures herein are particularly suitable for use in articles such as diapers, incontinence pads or garments, clothing shields, and the like.

In its simplest form, an absorbent article of the present invention need only include a backing sheet, typically relatively liquid-impervious, and one or more absorbent foam structures associated with this backing sheet. The absorbent foam structure and the backing sheet will be associated in such a manner that the absorbent foam structure is situated between the backing sheet and the fluid discharge region of the wearer of the absorbent article. Liquid impervious backing sheets can comprise any material, for example polyethylene or polypropylene, having a caliper of about 1.5 mils (0.038 mm), which will help retain fluid within the absorbent article.

More conventionally, the absorbent articles herein will also include a liquid-pervious topsheet element which covers the side of the absorbent article that touches the skin of the wearer. In this configuration, the article includes an absorbent core comprising one or more absorbent foam structures of the present invention positioned between the backing sheet and the topsheet. Liquid-pervious topsheets can comprise any material such as polyester, polyolefin, rayon and the like which is substantially porous and permits body fluid to readily pass therethrough and into the underlying absorbent core. The topsheet material will preferably have no affinity for holding aqueous body fluids in the area of contact between the topsheet and the wearer's skin.

The absorbent core of the absorbent article embodiments of this invention can consist solely of one or more of the foam structures herein. For example, the absorbent core can comprise a single unitary piece of foam shaped as desired or needed to best fit the type of absorbent article in which it is to be used. Alternatively, the absorbent core can comprise a plurality of foam pieces or particles which can be adhesively bonded together or which can simply be constrained into an unbonded aggregate held together by an overwrapping of envelope tissue or by means of the topsheet and backing sheet of the absorbent article.

The absorbent core of the absorbent articles herein can also comprise other, e.g., conventional, elements or materials in addition to one or more absorbent foam structures of the present invention. For example, absorbent articles herein can utilize an absorbent core which comprises a combination, e.g., an air-laid mixture, of particles or pieces of the absorbent foam structures herein and conventional absorbent materials such as a) wood pulp or other cellulosic fibers, and/or, b) particles or fibers of polymeric gelling agents.

In one embodiment involving a combination of the absorbent foam herein and other absorbent materials, the absorbent articles herein can employ a multi-layer absorbent core configuration wherein a core layer containing one or more foam structures of this invention can be used in combination with one or more additional separate core layers comprising conventional absorbent structures or materials. Such conventional absorbent structures or materials, for example, can include air-laid or wet-laid webs of wood pulp or other cellulosic fibers. Such conventional structures can also comprise conventional, e.g., large cell, absorbent foams or even sponges. The conventional absorbent structures used with the absorbent foam herein can also contain, for example up to 80% by weight, of particles or fibers of polymeric gelling agent of the type commonly used in absorbent articles that are to acquire and retain aqueous body fluids. Polymeric gelling agents of this type and their use in absorbent articles are more fully described in U.S. Pat. Re. No. 32,649 (Brandt et al), reissued Apr. 19, 1988, which is incorporated by reference.

One preferred type of absorbent article herein is one which utilizes a multi-layer absorbent core having fluid handling layer positioned in the fluid discharge region of the wearer of the article. This fluid-handling layer can be in the form of a high loft nonwoven, but is preferably in the form of a fluid acquisition/distribution layer comprising a layer of modified cellulosic fibers, e.g., stiffened curled cellulosic fibers, and optionally up to about 10% by weight of this fluid acquisition/distribution layer of polymeric gelling agent. The modified cellulosic fibers used in the fluid acquisition/distribution layer of such a preferred absorbent article are preferably wood pulp fibers which have been stiffened and curled by means of chemical and/or thermal treatment. Such modified cellulosic fibers are of the same type as are employed in the absorbent articles described in U.S. Pat. No. 4,935,622 (Lash et al), issued Jun. 19, 1990, which is incorporated by reference.

These multi-layer absorbent cores also comprise a second, i.e., lower, fluid storage/redistribution layer comprising a foam structure of the present invention. For purposes of this invention, an "upper" layer of a multi-layer absorbent core is a layer which is relatively closer to the body of the wearer, e.g., the layer closest to the article topsheet. The term "lower" layer conversely means a layer of a multi-layer absorbent core which is relatively further away from the body of the wearer, e.g., the layer closest to the article backsheet. This lower fluid storage/redistribution layer is typically positioned within the absorbent core so as to underlie the (upper) fluid-handling layer and be in fluid communication therewith. Absorbent articles which can utilize the absorbent foam structures of this invention in a lower fluid storage/redistribution layer underlying an upper fluid acquisition/distribution layer containing stiffened curled cellulosic fibers are described in greater detail in the U.S. Pat. No. 5,147,345 (Young et al), issued Sep. 15, 1992 which is incorporated by reference.

As indicated hereinbefore, the fluid handling and mechanical characteristics of the specific absorbent foam structures herein render such structures especially suitable for use in absorbent articles in the form of disposable diapers. Disposable diapers comprising the absorbent foam structures of the present invention can be made by using conventional diaper making techniques, but by replacing or supplementing the wood pulp fiber web ("airfelt") or modified cellulosic core absorbents typically used in conventional diapers with one or more foam structures of the present invention. Foam structures of this invention can thus be used in diapers in single layer or, as noted hereinbefore, in various multiple layer core configurations. Articles in the form of disposable diapers are more fully described in U.S. Pat. Re. No. 26,151 (Duncan et al), issued Jan. 31, 1967; U.S. Pat. No. 3,592,194 (Duncan), issued Jul. 13, 1971; U.S. Pat. No. 3,489,148 (Duncan et al), issued Jan. 13, 1970; U.S. Pat. No. 3,860,003, issued Jan. 14, 1975; and U.S. Pat. No. 4,834,735 (Alemany et al), issued May 30, 1989; all of which are incorporated by reference.

Figure 5:
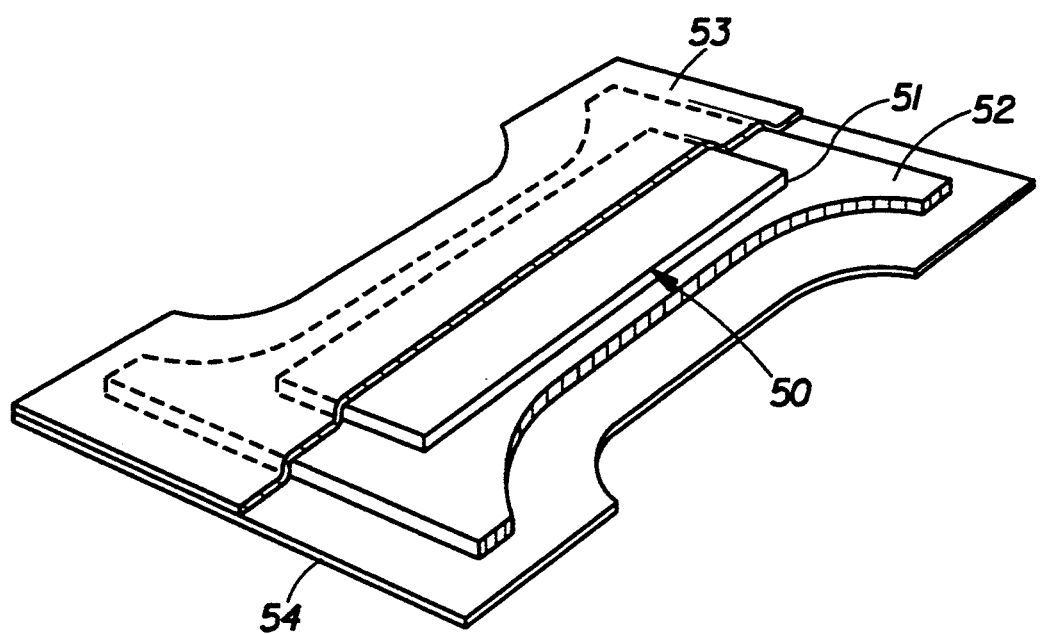
FIG. 5 of the drawings is a cutaway depiction of a disposable diaper which utilizes the absorbent polymeric foam of the present invention as an hourglass-shaped fluid storage/distribution component in an absorbent diaper core of dual-layer configuration.

A preferred disposable diaper embodiment of this invention is illustrated by FIG. 5 of the drawings. Such a diaper includes an absorbent core 50, comprising an upper fluid acquisition layer 51, and an underlying fluid storage/distribution layer 52 comprising an absorbent foam structure of this invention. A topsheet 53 is superposed and co-extensive with one face of the core, and a liquid impervious backsheet 54 is superposed and coextensive with the face of the core opposite the face covered by the topsheet. The backsheet most preferably has a width greater than that of the core thereby providing side marginal portions of the backsheet which extend beyond the core. The diaper is preferably constructed in an hourglass configuration.

Another preferred type of absorbent article which can utilize the absorbent foam structures of the present invention comprises form-fitting products such as training pants. Such form-fitting articles will generally include a nonwoven, flexible substrate fashioned into a chassis in the form of briefs or shorts. An absorbent foam structure according to the present invention can then be affixed in the crotch area of such a chassis in order to serve as an absorbent "core". This absorbent core will frequently be over-wrapped with envelope tissue or other liquid pervious, nonwoven material. Such core overwrapping thus serves as the "topsheet" for the form-fitting absorbent article.

The flexible substrate which forms the chassis of the form-fitting article can comprise cloth or paper or other kinds of nonwoven substrate or formed films and can be elasticized or otherwise stretchable. Leg bands or waist bands of such training pants articles can be elasticized in conventional fashion to improve fit of the article. Such a substrate will generally be rendered relatively liquid-impervious, or at least not readily liquid-pervious, by treating or coating one surface thereof or by laminating this flexible substrate with another relatively liquid-impervious substrate to thereby render the total chassis relatively liquid-impervious. In this instance, the chassis itself serves as the "backsheet" for the form-fitting article. Typical training pants products of this kind are described in U.S. Pat. No. 4,619,649 (Roberts), issued Oct. 28, 1986, which is incorporated by reference.

Figure 6:
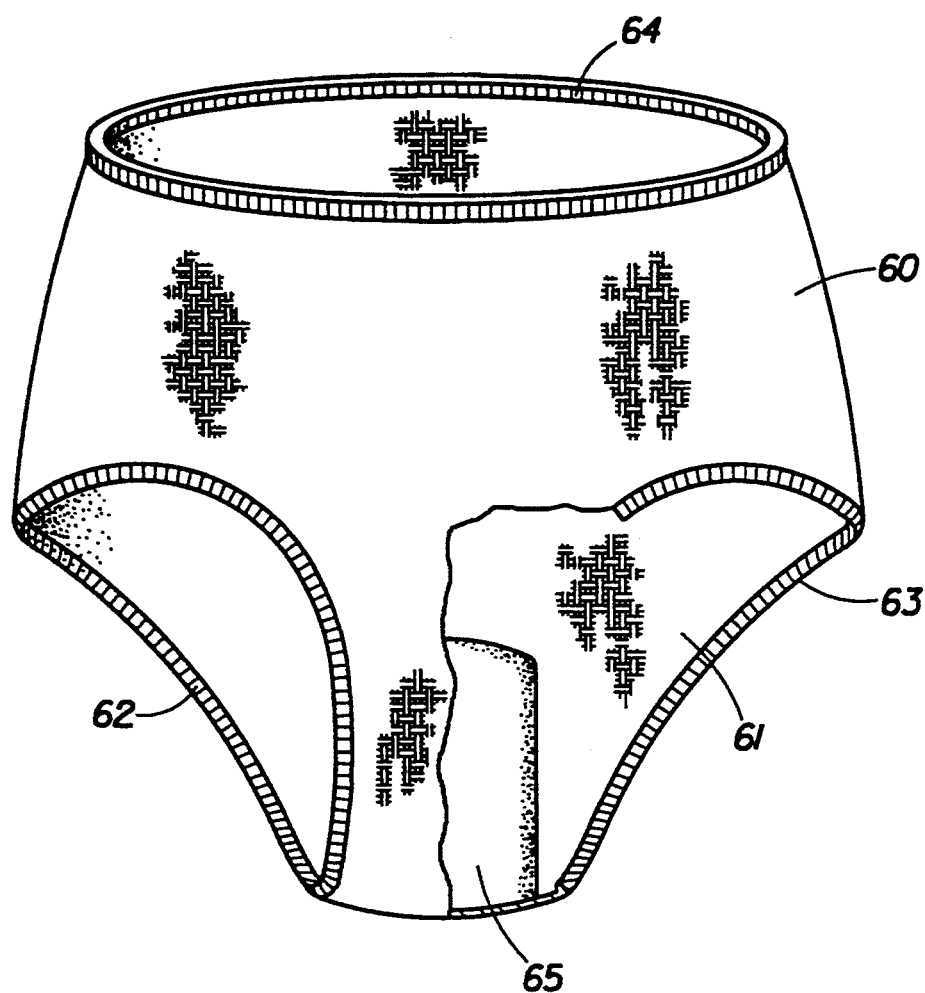
FIG. 6 of the drawings represents a cut-away view of a form-fitting article such as a disposable training pants product which employs an absorbent polymeric foam according to the present invention as an absorbent core.

A typical form-fitting article in the form of a disposable training pants product is shown in FIG. 6 of the drawings. Such a product comprises an outer layer 60 affixed to a lining layer 61 by adhesion along the peripheral zones thereof. For example, the inner lining 61 can be affixed to the outer layer 60, along the periphery of one leg band area 62, along the periphery of the other leg band area 63, and along the periphery of waistband area 64. Affixed to the crotch area of the article is a generally rectangular absorbent core 65 comprising an absorbent foam structure of the present invention.

TEST METHODS

In describing the present invention, a number of characteristics of the HIPE foam absorbent structures are set forth. Where reported, these characteristics can be determined using the following test fluids and test methods.

I) Test Fluids and Foam Sample Preparation

A) Test Fluid - Synthetic Urine

Several of the measurements described in the tests herein involve the use of a test fluid such as synthetic urine, ethanol, or 2-propanol (isopropyl alcohol). The synthetic urine utilized in a number of the tests described hereafter is made from a commercially available synthetic urine preparation manufactured by Jayco Pharmaceuticals (Mechanicsburg, Pa., 17055). This Jayco synthetic urine made from the preparation comprises KCl, 0.2%; $Na_2SO_4$, 0.2%; $NH_4H_2PO_4$, 0.085%; $(NH_4)_2HPO_4$, 0.015%; $CaCl_2*2H_2O$, 0.025%; and $MgCl_2*6H_2O$, 0.05%. (weight %'s) The synthetic urine samples are prepared according to the label instructions using distilled water. To aid dissolution, the Jayco salt mixture is slowly added to the water. The sample is filtered if necessary to remove any particulates. Any unused synthetic urine is discarded after one week. To improve visibility of the fluid, 5 drops of blue food color can be added per liter of synthetic urine solution. The Jayco synthetic urine utilized has a surface tension of 65 ±5 dynes/cm.

B) Foam Sample Preparation

A number of the following tests involve the preparation and testing of foam samples of a particular specified size. Unless otherwise specified, foam samples of the requisite size should be cut from larger blocks of foam using a sharp reciprocating knife saw. Use of this or equivalent type of foam cutting device serves to substantially eliminate sample edge flaws which could have an adverse impact on certain of the measurements made in carrying out the several test procedures hereafter set forth.

Sample size specification will also generally include a dimension for sample caliper or thickness. Caliper or thickness measurements for purposes of the present invention should be made when the foam sample is under a confining pressure of 0.05 psi (350 Pa). All measurements of foam density and dry weight are usually carried out after the foam sample has been water washed and dried, as described hereafter.

II) Determination of Properties, Features or Characteristics of Foam

A. Collapsed State

1) Expansion Pressure

This test directly measures the stored energy in the collapsed foam. The stored energy of the collapsed foam is released when it is flooded with an amount of water greater than its free absorbent capacity. Expansion pressure is measured while the fully wetted foam is being held by compressive forces at its collapsed caliper (thickness).

To conduct this test, a 23.8 mm. diameter cylinder of the collapsed foam is carefully cut out using a punch. The caliper of this cut sample is measured with a strain gauge (e.g., Ono-Sokki Model EG-225) to the nearest 0.005 mm. In performing the stress relaxation test, a Rheometrics Model RSA II is used having a parallel plate assembly capable of retaining liquid. This parallel plate assembly comprises a bottom cup plate having a cylindrical chamber with an inside diameter of 29 mm., and a top plate having a circular member with a diameter of 25 mm.

The cut, dry sample is placed within the chamber of the bottom cup plate and centered under the circular member of the top plate. The entire assembly/sample is then equilibrated at 88° F. (31.1° C.) for at least 10 minutes, with the top plate being adjusted to rest on the cut sample with a force of about 10 g. The Rheometrics Model RSA II is programmed to run a stress-relaxation test at 0.5% strain (in compression) at 88° F. (31.1° C.). While monitoring stress as a function of time, enough water having a temperature of 88° F. (31.1° C.) is quickly added to the bottom cup plate using a syringe to insure complete saturation of the cut sample (e.g., 3 mL in 1 second). The pressure the cut sample exerts on the plates as it tries to expand (i.e. its expansion pressure) is recorded for at least 15 minutes after the point at which the water is added; the value at 5 minutes is recorded as the expansion pressure of the cut sample.

2) Capillary Suction Specific Surface Area

Capillary suction specific surface area of the foam can be determined from the equilibrium weight uptake of a test liquid of known low surface tension. In this instance. absolute ethanol (flash point is 10° C.) is used.

To conduct the test, a tared foam sample strip of suitable dimensions (e.g., >35 cm long×2 cm wide×0.25 cm thick) is equilibrated at 22°±2° C., is positioned vertically and at one end is immersed 1–2mm into a reservoir of the ethanol using a lab jack. The ethanol is allowed to wick up the foam strip to its equilibrium height which should be less than the sample length. The ethanol-containing strip is then weighed to determine the weight of total ethanol uptake. During this procedure the sample should be shielded, for example with a capped glass cylinder, to prevent ethanol evaporation. The ethanol is then allowed to evaporate from the foam sample which is then water washed, dried and weighed.

Specific surface area of the foam sample can be calculated from the following formula:

$$S_c = \frac{M_e G L_n}{M_n \gamma_e}$$

where $S_c$=capillary suction specific surface area in cm²/gm; $M_e$=mass of liquid uptake of ethanol in gms; G=the gravitational constant which is 980 cm/sec²; $L_n$=total length of wet sample in cm; $M_n$=mass of dry sample in gm; and $\gamma_e$=surface tension of ethanol which is 22.3 dynes/cm. Values obtained can then be divided by 10000 cm²/m² to provide capillary suction specific surface area in m²/g.

3) Foam Density

One procedure which can be used to determine foam density is that described in ASTM Method No. D3574-86, Test A, which is designed primarily for the testing of urethane foams but which can also be utilized for measuring the density of the preferred HIPE-type foams of the present invention. In particular, density measurements made according to this ASTM procedure are carried out on foam samples which have been preconditioned in a certain manner as specified in that test.

Density is determined by measuring both the dry mass of a given foam sample (after water washing and drying) and its volume at 22°±2° C. Volume determinations on larger foam samples are calculated from measurements of the sample dimensions made under no confining pressure. Dimensions of smaller foam samples can be measured using a dial-type gauge using a pressure on the dial foot of 350 Pa (0.05 psi).

Density is calculated as mass per unit volume. For purposes of this invention, density is generally expressed in terms of g/cm³.

B. Expanded State

1) Density Upon Saturation with Synthetic Urine

In this measurement, the foam sample is saturated at 88° F. (31.1° C.) to its free absorbent capacity with Jayco synthetic urine. The volume is measured in this fully expanded state and the dry mass of the sample is measured after water washing and drying. The density upon saturation with synthetic urine is thus calculated as dry mass per wet volume, expressed in terms of g/cm³.

2) Available Pore Volume

A procedure for determining available pore volume involves the measurement of the amount of 2-propanol (flash point 12° C.) which can be introduced into the structure of an absorbent foam sample. Equipment and materials used in making such a measurement are equilibrated at 22°±2° C. Measurements are also performed at this temperature.

Dry foam samples are cut into 1 in² (6.5 cm²) circular surface area×0.1 inch (0.25 cm) thick cylinders or the equivalent. Such cylindrical samples can be prepared by using a sharp punch 1.13 inches (2.87 cm) in diameter on a 0.1 inch (0.25 cm) sheet of foam. The dry foam samples (after water washing and drying) are each weighed to determine a dry weight (DW). Three of such samples are weighed to determine an average dry weight (DW).

The Measured Free Capacity (MFC) of these samples is then determined by the following steps:

a) The foam samples are immersed in the 2-propanol in a crystallizing dish and allowed to saturate. At this point the sample may be squeezed a few times to expel air.

b) Each sample is removed without squeezing 2-propanol out of it. Excess fluid is allowed to drip off of the sample in the flat position for about 30 seconds. Each sample is then weighed wet to determine a wet weight (WW).

c) Steps a) and b) are repeated two more times and an average wet weight (WW) is calculated.

Measured Free Capacity (MFC, g/g) is the weight of 2-propanol in the saturated Foam per unit mass of dry foam. MFC is calculated according to the formula $$MFC = \frac{[WW(g) - DW(g)]}{DW(g)}$$

Available pore volume is then calculated by dividing the MFC of the foam for 2-propanol by the density of 2-propanol which is 0.785 g/mL. This gives an available pore volume for the foam in mL/g.

3) Resistance to Compression Deflection

Resistance to compression deflection can be quantified for purposes of this invention by measuring the amount of strain (% caliper reduction) produced in a foam sample, which has been saturated and fully expanded with synthetic urine, after stress in the form of a 0.74 psi (5.1 kPa) confining pressure has been applied to the sample.

The foam samples, Jayco synthetic urine and equipment used to make measurements are all equilibrated to a temperature of 88° F. (31.1° C.). Measurements are also performed at this temperature.

A foam sample sheet in its collapsed state is saturated to its free absorbent capacity with Jayco synthetic urine. After 2 minutes, a cylinder having a 1 in² (6.5 cm²) circular surface area is punched out of the saturated, fully expanded sheet. A dial-type gauge suitable for making caliper measurements is positioned on the sample. Any gauge fitted with a foot having a circular surface area of at least 1 in² (6.5 cm²) and capable of measuring caliper dimensions to 0.001 in (0.025 mm) can be employed. Examples of such gauges are an Ames model 482 (Ames Co.; Waltham, Mass.) or an Ono-Sokki model EG-225 (Ono-Sokki Co., Ltd.; Japan).

A force is then applied to the foot so that the saturated foam sample on the screen is subjected to a confining pressure of 0.74 psi (5.1 kPa) for 15 minutes. At the end of this time, the dial gauge is used to measure the change in sample caliper which occurs as a consequence of the application of the confining pressure. From the initial and final caliper measurements, a percent strain induced can be calculated for the sample.

4) Recovery From Compression Deflection

To test recovery from compression deflection, foam samples similar to those prepared for the Resistance to Compression Deflection test (see II(B)(3) above) are used.

Using a dial-type gauge, a test sample saturated to its free absorbent capacity in Jayco synthetic urine at 88° F. (31.1° C.) is compressed within 10 seconds to 50% of its original thickness and maintained in the compressed state for 1 minute. The pressure is then released, and the foam is allowed to recover thickness for 1 minute in the presence of the expelled fluid. The percent recovery is based on the original height of the uncompressed foam.

C. Collapsed or Expanded States

1) Flexibility

Foam flexibility can be quantified by referencing a test procedure which is a modification of the ASTM D 3574-86, 3.3 test used to determine flexibility of cellular organic polymeric foam products. Such a modified test utilizes a foam sample which is 7×0.8×0.8 cm when saturated to its free absorbent capacity with Jayco synthetic urine at 88° F. (31.1° C.). It is important that the cutting process used to make these samples does not introduce edge defects in the foam strip. The synthetic urine-saturated foam strip is bent around a 0.8 cm diameter cylindrical mandrel at a uniform rate of 1 lap in 5 seconds until the ends of the strip meet. The foam is considered flexible if it does not tear or break during this test, i.e., if it passes one bending cycle.

D. Determination of Fluid Handling Characteristics

1) Free Absorbent Capacity

In this test, a foam sample is saturated at 88° F. (31.1° C.) with Jayco synthetic urine. The same procedure described in II(B)(2) above for Available Pore Volume is then used to measure the no-load (free) absorbent capacity.

2) Vertical Wicking Rate and Vertical Wicking Absorbent Capacity

Vertical wicking rate and vertical wicking absorbent capacity are measures of the ability of a dry foam to wick fluid vertically from a reservoir. The time required for the fluid front to wick through a 5 cm vertical length of a strip of foam is measured to give a vertical wicking rate. After fluid wicks to its equilibrium height, the amount of fluid held by the foam strip at a particular vertical wicking height (e.g., 4.5 inches or 11.4 cm) is determined to give a vertical wicking absorbent capacity.

Jayco synthetic urine colored with blue food coloring is used in the following methods to determine vertical wicking rate and vertical wicking absorbent capacity. In this test procedure, the materials are equilibrated at 37° C. and the test is performed at the same temperature.

A strip of foam approximately 70 cm long×2 cm wide×0.25 cm thick is supported vertically with one end immersed 1 to 2 mm into a reservoir of synthetic urine. The liquid is allowed to wick up the foam strip to its equilibrium height (e.g., about 18 hours), which should be less than the sample length. During this procedure, the sample should be shielded, for example with a capped glass cylinder, to prevent evaporation.

The time needed to wick 5 cm is used as a measure of vertical wicking rate. The equilibrium wet weight can be recorded and used to calculate Adhesion Tension, as described below.

The sample is quickly removed and placed on a non-absorbent surface where it is cut into 1 inch (2.54 cm) pieces using a tool sharp enough not to compress the foam sample. Each piece is weighed, washed with water, dried and then reweighed. The absorbent capacity is calculated for each piece. The absorbent capacity of the 1 inch segment centered at 4.5 inches (11.4 cm) wicking height is the parameter most desirably determined.

3) Adhesion Tension

The adhesion tension exhibited by hydrophilized foam samples which imbibe test fluids via capillary suction is the product of the surface tension, $\gamma$, of the test fluid times the cosine of the contact angle, $\Theta$, exhibited by the test fluid in contact with the interior surfaces of the foam sample. Adhesion tension can be determined experimentally by measuring the equilibrium weight uptake by capillary suction exhibited by two test samples of the same foam using two different test liquids. In the first step of such a procedure, specific surface area of the foam sample is determined using ethanol as the test fluid as described in II(A)(2) above for Capillary Suction Specific Surface Area.

The capillary suction uptake procedure is then repeated in identical manner to the ethanol procedure except that: (a) Jayco synthetic urine is used as the test fluid; (b) the test is carried out at 37° C.; and (c) a foam sample strip $\geq$70 cm long×2 cm wide×0.25 cm thick is used. The contact angle of the synthetic urine can then be calculated as follows from the known specific surface area and the synthetic urine uptake data:

$$\cos\theta_U = \frac{M_U G L_N}{M_N \gamma_U S_c}$$

where $\Theta_U$=contact angle of Jayco synthetic urine in degrees; $M_U$=mass of liquid uptake of Jayco synthetic urine in gms; G=gravitational constant which is 980 cm/sec²; $M_N$=mass of dry foam sample in gm; $\gamma_U$=surface tension of Jayco urine which is $\neq$65 dynes/cm; $S_c$=specific surface area of the foam sample in cm²/gm as determined by the ethanol uptake procedure; and $L_n$=length of the wet foam sample in cm.

When a surfactant is present (on the foam sample surfaces and/or in the advancing test liquid), characterization of the advancing liquid front is defined by applying the adhesion tension (AT) equation:

$$AT = \frac{M_T GL_N}{M_N S_c}$$

wherein $M_T$ is the mass of the test liquid taken up by the foam sample, and G, $L_N$, $M_N$, and $S_c$ are as defined before. [See Hodgson and Berg, *J. Coll. Int. Sci.*, 121(1), 1988, pp. 22–31]

In determining adhesion tension for any given test liquid, no assumption is made of the numerical value of the surface tension at any point in time so that possible changes in surfactant concentration on the sample surfaces and/or in the advancing liquid during wicking are immaterial. The experimental value of adhesion tension ($\gamma \cos\Theta$) is especially useful when viewed as a percentage of the maximum adhesion tension which is the surface tension of the test liquid (e.g., the maximum adhesion tension using Jayco synthetic urine would be [65±5] [cos 0°]=65±5 dynes/cm).

PGE ANALYTICAL METHODS

A. Interfacial tension (IFT) method (Spinning Drop)

IFT can be measured using a Kruss SITE 04 Spinning Drop Tensiometer or any equivalent spinning drop tensiometer operating under the same principles. See Cayias et al, *Absorption at Interfaces*, edited by Mittal, ACS Symposium Series 8 (1975), pp. 234–47, and Aveyard et al, *J. Chem. Soc. Faraday Trans.*, Vol. 1 (1981), pp. 2155–68, for general descriptions of spinning drop IFT methods. For each IFT measurement, a drop of the oil phase containing the PGE (typically 5 microliters) is injected into the spinning capillary tube of the tensiometer which contains the aqueous phase pre-equilibrated to 50° C. The spinning rate of the tube is increased sufficiently to elongate the drop into a cylindrical shape such that its ratio of length:diameter is greater than 4:1. The elongated drop is allowed to equilibrate at 50° C. until equilibrium is reached (i.e. no further change in drop diameter) or until approximately 30 minutes have elapsed. Preferably, the elongated drop is of uniform diameter (except at the hemispherical ends) and its interface with the aqueous solution is essentially free of deposited material and/or smaller droplets. If not, then a region of the elongated drop that is essentially free of deposits, has a length:diameter ratio of greater than 4:1 and a minimum diameter (if regions of different diameter are present) is chosen for the measurement. The interfacial tension ($\gamma$) is calculated from the measured radius (r, ½ the cylindrical diameter), the angular velocity ($\omega$; $2\pi$n, where n is the frequency of rotation of the tube), and the density difference between the oil and aqueous phases ($\Delta$ p), using the following equation:

$$\gamma = 0.25\ r^3 \Delta p\ \omega^2$$

Calibration of this system is periodically checked by measuring the IFT between n-octanol and water (8.5 dynes/cm at 20° C.).

The oil phase used for these measurements is typically prepared by adding 10 parts of the PGE to 100 parts of a monomer mixture containing styrene, divinylbenzene (55% technical grade) and 2-ethylhexylacrylate in a weight ratio of 2:2:6. This mixture is mechanically agitated to effect dissolution of the PGE. This oil phase mixture is allowed to stand overnight at ambient temperature so that materials (typically free polyglycerols) which are insoluble or precipitate out of solution can settle. After centrifugation, the supernatant is separated from any sediment. The supernatant is used as is and diluted (sequentially if necessary) with additional monomer mixture to yield emulsifier solutions having lower concentrations. In this fashion, solutions having nominal PGE concentrations ranging from approximately 9% to 0.01% or lower can be prepared. The water phase used for this measurement is an 0.90M aqueous solution of calcium chloride (approximate pH 6) prepared by dissolving $CaCl_2 \cdot 2H_2O$ in distilled water.

A series of IFT measurements are made by varying the concentration of PGE in the oil phase up to at least 3%. A smooth curve is drawn through a log-log plot of IFT values as a function of PGE concentration in the oil phase. A minimum IFT value is then estimated from the curve.

B. Polyglycerol Distribution

The distribution of polyglycerols in a sample can be determined by capillary supercritical fluid chromatography. See Chester et al, *J. High Res. Chrom. & Chrom. Commun.*, Vol. 9 (1986), p. 178 et seq. In this method, the polyglycerols in the sample are converted to the respective trimethylsilyl ethers by reaction with bis(-trimethylsilyl)-trifluoroacetamide. The trimethylsilyl ethers are separated and then quantified by capillary supercritical fluid chromatography using flame ionization detection. The trimethylsilyl ethers elute from the polydimethylsiloxane stationary phase in order of increasing molecular weight. Peak identities are established by coupling the supercritical fluid chromatograph to a mass spectrometer. The relative distribution of polyglycerol species is calculated from peak areas in the chromatogram. Weight percentages are calculated by assuming that the flame ionization detection responds equally to all polyglycerol species in the sample.

C. Fatty Acid Composition (FAC)

The fatty acid composition of a sample of free fatty acids or fatty acid esters can be determined by high resolution capillary gas chromatography. See D'Alonzo et al, *J. Am. Oil Chem. Soc.*, Vol. 58 (1981), p. 215 et seq. In this method, the fatty acids in the sample are converted to fatty acid methyl esters that are then separated and quantified by high resolution capillary gas chromatography with flame ionization detection. The capillary column stationary phase (a stabilized polyethylene glycol) separates the methyl esters according to chain length and degree of unsaturation. Peak identities are established by comparison with known fatty acid standards. The relative distribution of fatty acid species is calculated from the peak areas in the chromatogram. Weight percentages are calculated by assuming the flame ionization detector responds equally to all fatty acid species in the sample.

EXAMPLES

Preparation of collapsed HIPE absorbent foams, the characteristics of such collapsed foams and utilization of these collapsed absorbent foams in disposable diapers are all illustrated by the following examples.

EXAMPLE I

This example illustrates the preparation of a collapsed HIPE foam falling within the scope of the present invention.

Emulsion Preparation

Anhydrous calcium chloride (36.32 kg) and potassium persulfate (568 g) are dissolved in 378 liters of water. This provides the water phase stream to be used in a continuous process for forming a HIPE emulsion.

To a monomer combination comprising styrene (1600 g), divinylbenzene 55% technical grade (1600 g), and 2-ethylhexylacrylate (4800 g) is added sorbitan laurate (960 g as SPAN ® 20). After mixing, this combination of materials is allowed to settle overnight. The supernatant is withdrawn and used as the oil phase in a continuous process for forming a HIPE emulsion. (About 75 g of a sticky residue is discarded.)

At an aqueous phase temperature of 48°–50° C. and an oil phase temperature of 22° C., separate streams of the oil phase and water phase are fed to a dynamic mixing apparatus. Thorough mixing of the combined streams in the dynamic mixing apparatus is achieved by means of a pin impeller. At this scale of operation, an appropriate pin impeller comprises a cylindrical shaft of about 21.6 cm in length with a diameter of about 1.9 cm. The shaft holds 4 rows of pins, 2 rows having 17 pins and 2 rows having 16 pins, each having a diameter of 0.5 cm extending outwardly from the central axis of the shaft to a length of 1.6 cm. The pin impeller is mounted in a cylindrical sleeve which forms the dynamic mixing apparatus, and the pins have a clearance of 0.8 mm from the walls of the cylindrical sleeve.

A spiral static mixer is mounted downstream from the dynamic mixing apparatus to provide back pressure in the dynamic mixer and to provide improved incorporation of components into the emulsion that is eventually formed. Such a static mixer is 14 inches (35.6 cm) long with a 0.5 inch (1.3 cm) outside diameter. The static mixer is a TAH Industries Model 070-821, modified by cutting off 2.4 inches (6.1 cm).

The combined mixing apparatus set-up is filled with oil phase and water phase at a ratio of 2 parts water to 1 part oil. The dynamic mixing apparatus is vented to allow air to escape while filling the apparatus completely. The flow rates during filling are 1.127 g/sec oil phase and 2.19 cm³/sec water phase.

Once the apparatus set-up is filled, agitation is begun in the dynamic mixer, with the impeller turning at 1800 RPM. The flow rate of the water phase is then steadily increased to a rate of 35.56 cm³/sec over a time period of 130 sec. The back pressure created by the dynamic and static mixers at this point is 7.5 PSI (51.75 kPa). The impeller speed is then steadily decreased to a speed of 1200 RPM over a period of 60 sec. The back pressure drops to 4.5 PSI (31.05 kPa). At this point, the impeller speed is instantly increased to 1800 RPM. The system back pressure remains constant thereafter at 4.5 PSI (31.05 kPa).

Polymerization of the Emulsion

The formed emulsion flowing from the static mixer at this point is collected in Rubbermaid Economy Cold Food Storage Boxes, Model 3500. These boxes are constructed of food grade polyethylene and have nominal dimensions of 18"×26"×9" (45.7 cm×66 cm 22.9 cm). The true inside dimensions of these boxes are 15"×23"×9" (38.1 cm×58.4 cm×22.9 cm). These boxes are pretreated with a film of a solution comprising a 20% solution of SPAN ® 20 in an equal weight solvent mixture of xylene and 2-propanol. The solvent mixture is allowed to evaporate to leave only the SPAN ® 20. Forty-seven liters of emulsion are collected in each box.

The emulsion-containing boxes are kept in a room maintained at 65° C. for 18 hours to bring about polymerization of the emulsion in the boxes to thereby form polymeric foam.

Foam Washing and Dewatering

After curing is complete, the wet cured foam is removed from the curing boxes. The foam at this point contains about 30–40 times the weight of polymerized material (30–40X) of the residual water phase containing dissolved emulsifiers, electrolyte and initiator. The foam is sliced with a sharp reciprocating saw blade into sheets which are 0.350 inches (0.89 cm) in caliper. These sheets are then subjected to compression in a series of 3 nip rolls which gradually reduce the residual water phase content of the foam to about 6 times (6X) the weight of the polymerized material. At this point, the sheets are then resaturated with a 1% $CaCl_2$ solution at 60° C., are squeezed in a nip to a water phase content of about 10X, resaturated with the 1% $CaCl_2$ solution at 60° C., and then squeezed again in a nip to a water phase content of about 10X.

The foam sheets, which now contain about 10X of what is essentially a 1% $CaCl_2$ solution are passed through a final nip equipped with a vacuum slot. The last nip reduces the $CaCl_2$ solution content to about 5 times (5X) the weight of polymer. The foam remains compressed after the final nip at a caliper of about 0.080 in. (0.2 cm). The foam is then dried in an air circulating oven set at about 60° C. for about three hours. Such drying reduces the moisture content to about 5–7% by weight of polymerized material. At this point, the foam sheets have a caliper of about 0.075 in. (0.19 cm) and are very drapeable. The foam also contains about 11% by weight of residual sorbitan laurate emulsifier and about 5% by weight (anhydrous basis) of residual hydrated calcium chloride. In the collapsed state, the density of the foam is about 0.17 g/cm³. When expanded in Jayco synthetic urine, its free absorbent capacity is about 30.2 mL/g. The expanded foam has a capillary suction specific surface area of about 2.24 m²/g, a pore volume of about 31 mL/g, a number average cell size of about 15 microns, an adhesion tension of about 35 dynes/cm, and a vertical wicking absorbent capacity of about 26.7 mL/g or about 88% of its free absorbent capacity.

EXAMPLE II

Figure 7:
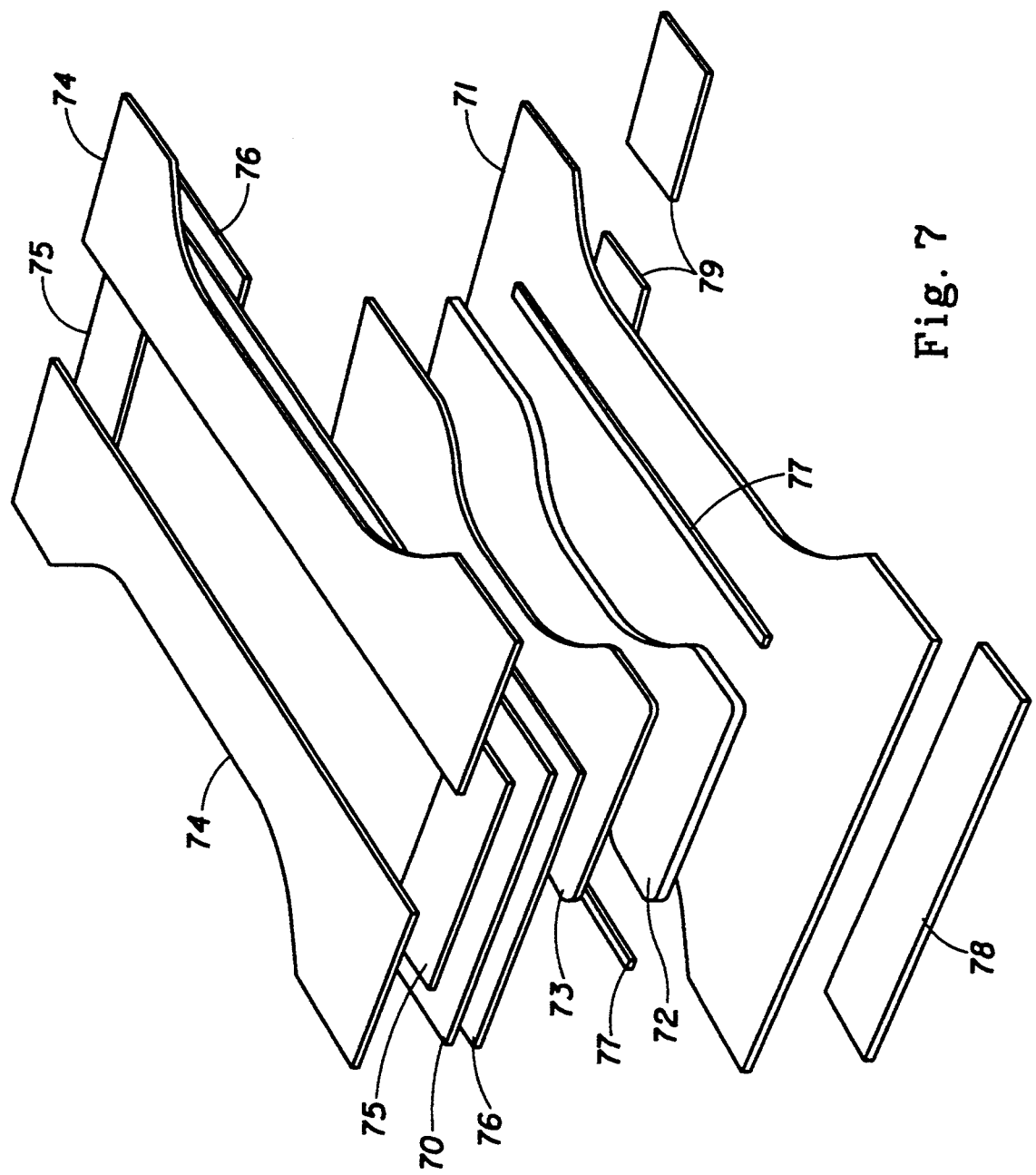
FIG. 7 of the drawings represents a blown-apart view of the components of a diaper structure also of dual layer core configuration having an hourglass-shaped fluid acquisition layer overlying an absorbent foam fluid storage/distribution layer with a modified hourglass shape.

A disposable diaper is prepared using the configuration and components shown in expanded and blown-apart depiction in FIG. 7. Such a diaper comprises a thermally bonded polypropylene topsheet 70, a fluid-impervious polyethylene backing sheet 71, and a dual layer absorbent core positioned between the topsheet and the backing sheet. The dual layer absorbent core comprises a modified hourglass-shaped, fluid storage/-redistribution layer 72 comprising the collapsed HIPE foam of the Example I type positioned below a modified-hourglass shaped fluid acquisition layer 73. The topsheet contains two substantially parallel barrier leg cuff strips 74 with elastic. Affixed to the diaper backsheet are two rectangular elasticized waistband members 75. Also affixed to each end of the polyethylene backsheet are two waistshield elements 76 constructed of polyethylene. Also affixed to the backsheet are two parallel leg elastic strips 77. A sheet of polyethylene 78 is affixed to the outside of the backsheet as a dedicated fastening surface for two pieces 79 of Y-tape which can be used to fasten the diaper around the wearer.

The acquisition layer of the diaper core comprises a 92%/8% wet-laid mixture of stiffened, twisted, curled cellulosic fibers and conventional non-stiffened cellulosic fibers. The stiffened, twisted, curled cellulosic fibers are made from southern softwood kraft pulp (Foley fluff) which has been crosslinked with glutaraldehyde to the extent of about 2.5 mole percent on a dry fiber cellulose anhydroglucose basis. The fibers are crosslinked according to the "dry crosslinking process" as described in U.S. Pat. No. 4,822,453 (Dean et al), issued Apr. 18, 1989.

These stiffened fibers are similar to the fibers having the characteristics described as follows in Table II.

Table II

Stiffened, Twisted, Curled Cellulose (STCC) Fibers

Type=Southern softwood kraft pulp crosslinked with glutaraldehyde to the extent of 1.41 mole percent on a dry fiber cellulose anhydroglucose basis
Twist Count Dry=6.8 nodes/mm
Twist Count Wet=5.1 nodes/mm
2-Propanol Retention Value=24%
Water Retention Value=37%
Curl Factor=0.63

The conventional non-stiffened cellulose fibers used in combination with the STCC fibers are also made from Foley fluff. These non-stiffened cellulose fibers are refined to about 200 CSF (Canadian Standard Freeness).

The acquisition layer has an average dry density of about 0.07 g/cm$^3$, an average density upon saturation with synthetic urine, dry weight basis, of about 0.08 g/cm$^3$, and an average basis weight of about 0.03 g/cm$^2$. About 13 grams of the fluid acquisition layer are used in the diaper core. The surface area of the acquisition layer is about 46.8 in$^2$ (302 cm$^2$). It has a caliper of about 0.44 cm.

The fluid storage/redistribution layer of the diaper core comprises a modified hourglass-shaped piece of collapsed HIPE foam of the type described in Example I. About 13 grams of HIPE foam are used to form this storage/distribution layer which has a surface area of about 52.5 in$^2$ (339 cm$^2$) and a caliper of about 0.1 in (0.25 cm).

A diaper having this particular core configuration exhibits especially desirable and efficient utilization of the core for holding discharged urine and accordingly provides exceptionally low incidence of leakage when worn by an infant in the normal manner. Similar results can be obtained if air-laid stiffened fibers are substituted for the wet-laid stiffened fibers in the acquisition layer of the absorbent core.

EXAMPLE III

Figure 3A:
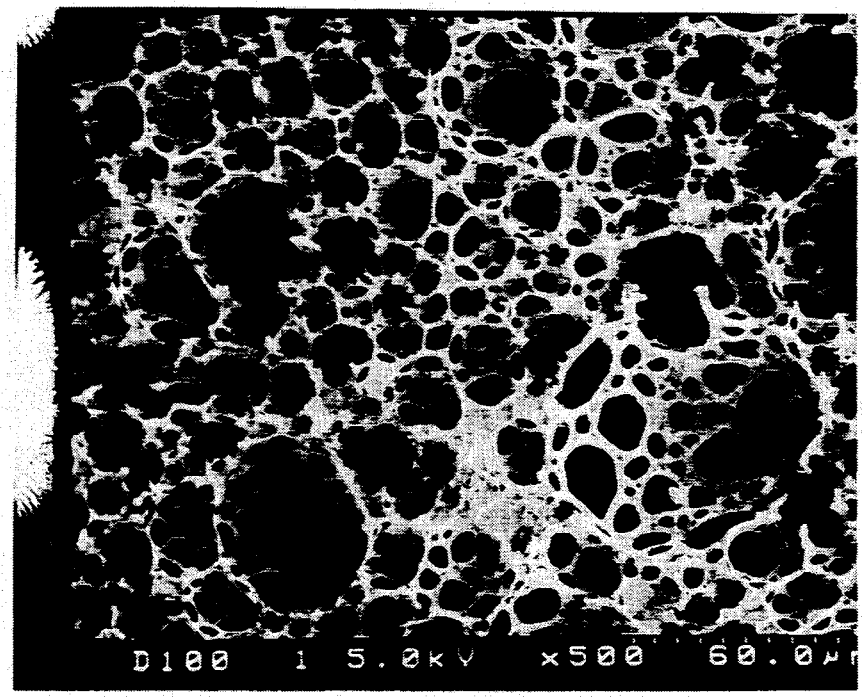
FIGS. 3a through 3d of the drawings are photomicrographs (500X magnification) of cut sections of absorbent polymeric foams prepared by polymerizing/curing a certain HIPE emulsion at different temperatures.
Figure 3B:
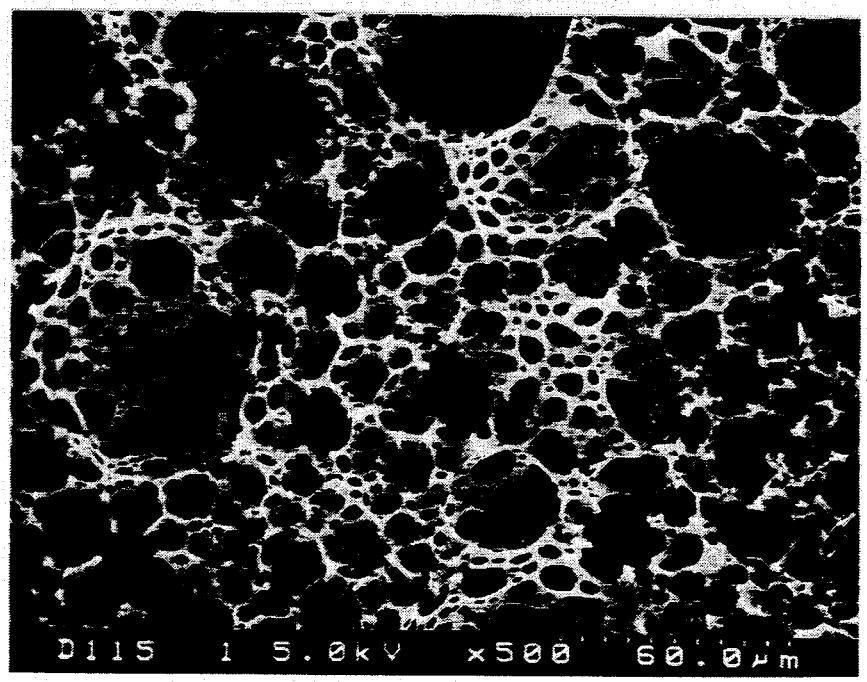
Figure 3C:
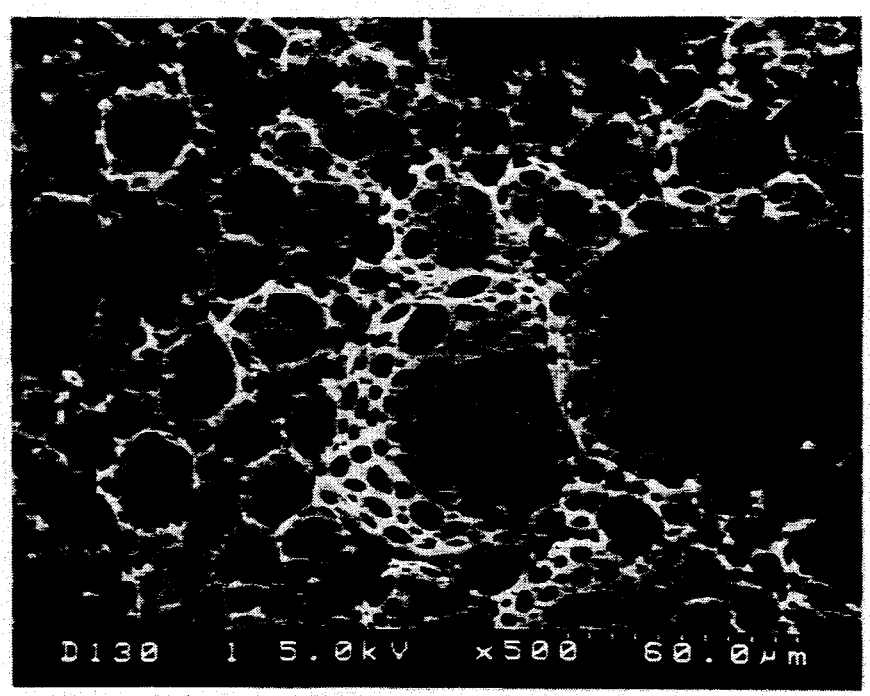
Figure 3D:
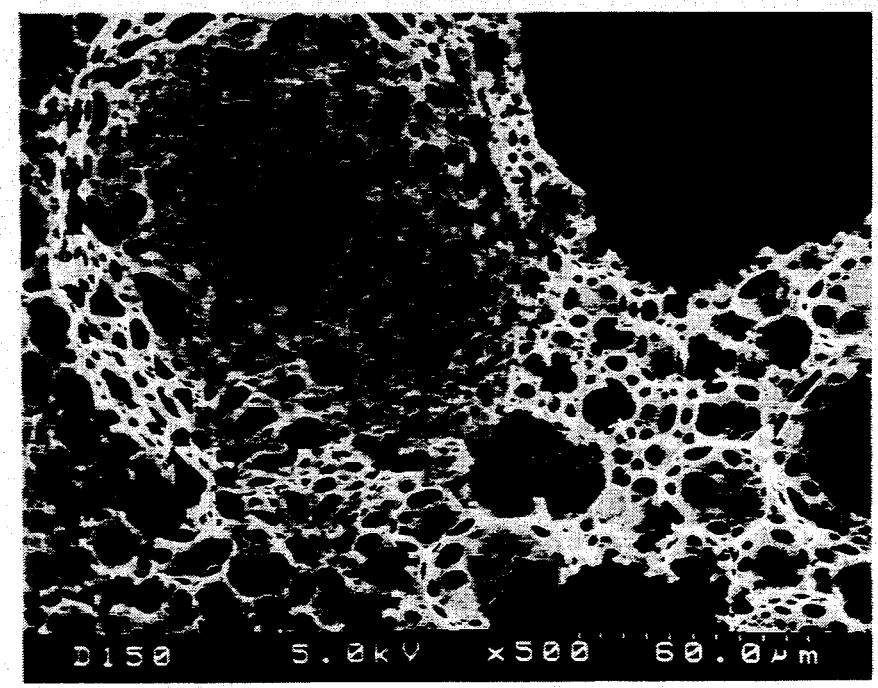

This example illustrates the benefit of using relatively low polymerization/cure temperatures to consistently reduce coalescense of water droplets in the HIPE emulsion and to consistently obtain collapsed polymeric foams according to the present invention, especially when SPAN ® 20 is the only emulsifier used in preparing the HIPE emulsion. In this example, a HIPE emulsion is prepared by a procedure similar to that of Example I, but using a different lot of SPAN ® 20 as the emulsifier. This HIPE emulsion is collected in a number of 1 pint plastic lidded jars. Four ovens are set at temperatures of 100° F. (37.8° C.), 115° F. (46.1° C.), 130° F. (54.4° C.), and 150° F. (65.6° C.), and several of the jars of HIPE emulsion are cured in each oven for 24 hours. A portion of the resultant cured foams are then washed with water and dried. Photomicrographs of the dried foams are then taken at magnifications of 50X, 500X and 1000X. FIGS. 3a through 3d are representative of such photomicrographs (500X magnification). Specifically, FIG. 3a shows a cut section of the 100° F. (37.8° C.) cured foam, FIG. 3b shows a cut section of the 115° F. (46.1° C.) cured foam, FIG. 3c shows a cut section of the 130° F. (54.4° C.) cured foam, and FIG. 3d shows a cut section of the 150° F. (65.6° C.) cured foam.

As shown in FIGS. 3a and 3b, the HIPE emulsions cured at lower temperatures (i.e. below about 50° C.) resulted in foam structures having smaller pores of relatively uniform size, i.e. the foam structures are relatively homogeneous. This suggests that there is reduced coalescence of the water droplets during curing of the HIPE emulsions. By contrast, as shown in FIGS. 3c and 3d, the HIPE emulsions cured at higher temperatures (i.e. above about 50° C.), resulted in foam structures having numerous larger pores and a relatively nonuniform pore size, i.e. the foam structures are essentially heterogeneous. This suggests significantly increased coalescence of the water droplets during curing of the HIPE emulsions.

The homogeneity of these cured foams in terms of cell sizes and coalescence can be graded qualitatively from the photomicrographs using the following scale:

| Grade | Description |
|---|---|
| 1 | massive coalescence, barely recognizable as foam |
| 2 | very bad coalescence, open voids, smeared struts |
| 3 | bad coalescence, thickened struts |
| 4 | moderate coalescence, some strut anomalies (thickened) |
| 5 | minor coalescence, no strut anomalies |
| 6 | minimal coalescence, no strut anomalies |
| 7 | well resolved homogeneous structure |

Several determinations are made for each of the cured foams based on the above scale, and are then averaged to obtain a mean grade for each of the cured foams, as shown in the following table:

| Cure Temperature | Mean Grade |
|---|---|
| 100° F. (37.8° C.) | 6.5 |
| 115° F. (46.1° C.) | 5.5 |
| 130° F. (54.4° C.) | 3.3 |
| 150° F. (65.6° C.) | 2.5 |

A portion of the above foam samples cured at 115° F. (46.1° C.), 130° F. (54.4° C.), and 150° F. (65.6° C.), are also evaluated for the ability to remain thin after washing with a salt solution, followed by pressing and drying. The cured foams are processed by washing with an aqueous solution of 1.0% calcium chloride, pressing to remove some of the water, and then oven drying (i.e. at about 150° F., 65.6° C.). Each of the dried foams is evaluated to determine whether it maintained its collapsed state, i.e. 10–30% of its original expanded thickness. The dried foam samples cured at 130° F. (54.4° C.), and 150° F. (65.6° C.) did not remain thin. By contrast, the dried foam samples cured at 115° F. (46.1° C.) did remain thin.

EXAMPLE IV

The following examples illustrate the preparation of HIPE foams using sorbitan laurate (SPAN ® 20) and polyglycerol fatty acid ester (PGE) or sorbitan palmitate (SPAN ® 40) co-emulsifier systems:

EXAMPLE IV A

Anhydrous calcium chloride (36.32 kg) and potassium persulfate (568 g) are dissolved in 378 liters of water. This provides the water phase stream used in forming the HIPE emulsion.

To a monomer mixture comprising styrene (1600 g), divinylbenzene (55% technical grade, 1600 g), and 2-ethylhexylacrylate (4800 g) is added sorbitan laurate (960 g as SPAN ® 20). To another half-size batch of the same monomer mixture is added PGE emulsifier (480 g) that imparts a minimum oil/water IFT of 0.09 dynes/cm. This PGE is obtained by esterifying polyglycerols with fatty acids in a weight ratio of 64:36 using sodium hydroxide as the catalyst at 210° C. under conditions of mechanical agitation, nitrogen sparging and gradually increasing vacuum, with subsequent phosphoric acid neutralization, cooling to about 60° C., and settling to reduce unreacted polyglycerol. The composition of the polyglycerols and fatty acids used in making the PGE are shown in the following table:

|  | Wt % |
| --- | --- |
| Polyglycerols |  |
| linear diglycerols | 63.5 |
| triglycerol or higher | 36.0 |
| cyclic diglycerols | 0.4 |
| Fatty Acids |  |
| C8 | — |
| C10 | — |
| C12 | 31.7 |
| C14 | 37.2 |
| C16 | 11.5 |
| C18:0 | 3.2 |
| C18:1 | 13.8 |
| C18:2 | 1.5 |

After mixing, each oil phase batch is allowed to settle overnight. The supernatant is withdrawn from each batch and mixed at a ratio of 2 parts of the SPAN ® 20 containing oil phase to 1 part of the PGE containing oil phase. (About 75 g of a sticky residue is discarded from each of the batches.)

At an aqueous phase temperature of 43° to 45° C. and an oil phase temperature of 22° C., separate streams of the oil and water phases are fed to a dynamic mixer in the form of a pin impeller. This pin impeller has a cylindrical shaft of about 21.6 cm in length with a diameter of about 1.9 cm. The shaft holds 4 rows of pins, two rows having 17 pins and two rows having 16 pins, each pin having a diameter of 0.5 cm and extending outwardly 1.6 cm from the central axis of the shaft. The pin impeller is mounted within a cylindrical sleeve with the pins having a clearance of 0.8 mm from the inner wall.

A spiral static mixer (14 in. long by ½ in. outside diameter, TAH Industries Model 070-821, modified by cutting off 2.4 inches) is mounted downstream from the dynamic mixer to provide back pressure in the dynamic mixer and to provide uniformity in the HIPE emulsion. The combined dynamic and static mixer apparatus is filled with oil and water phases at a ratio of 2 parts water to 1 part oil. The apparatus is vented to allow air to escape until filling of the apparatus is complete. The flow rates during filling are 3.0 g/sec oil phase and 4.5 cc/sec water phase.

Once the apparatus is filled, agitation is begun, with the impeller turning at 1100 RPM. The aqueous phase flow rate is then evenly ramped up to 46.5 cc/sec and the oil phase flow rate is evenly ramped down to 1.77 g/sec over a time period of 120 sec. The back pressure created by the dynamic and static mixers at this point is 4.9 psi. Over a time period of 30 sec, the impeller is slowed to 1000 RPM. When the back pressure drops to approximately 3 psi, the impeller speed is then instantly increased to 1800 RPM, and the back pressure increased to 5.5 psi. The water and oil flows are then adjusted to 47.8 cc/sec and 1.66 g/sec, respectively.

The HIPE emulsion is collected in molds (Rubbermaid Economy Cold Food Storage Boxes made of food grade polyethylene, Model 3500), having inside dimensions of 15 in. by 23 in. by 9 in. deep. The molds are pretreated with a film of a solution comprising 20% SPAN ® 20 in xylene which had been allowed to settle overnight to remove insolubles. The molds are preheated to facilitate the evaporation of the xylene and leave behind only the SPAN ® 20. 47 liters of HIPE emulsion are collected in each mold. The filled molds are kept in a room maintained at 65° C. for 18 hours to allow for curing. The cured foam is then washed with a 1% calcium chloride solution. The residual solution retained in the foam before drying is 5 times the weight of foam.

Figure 4:
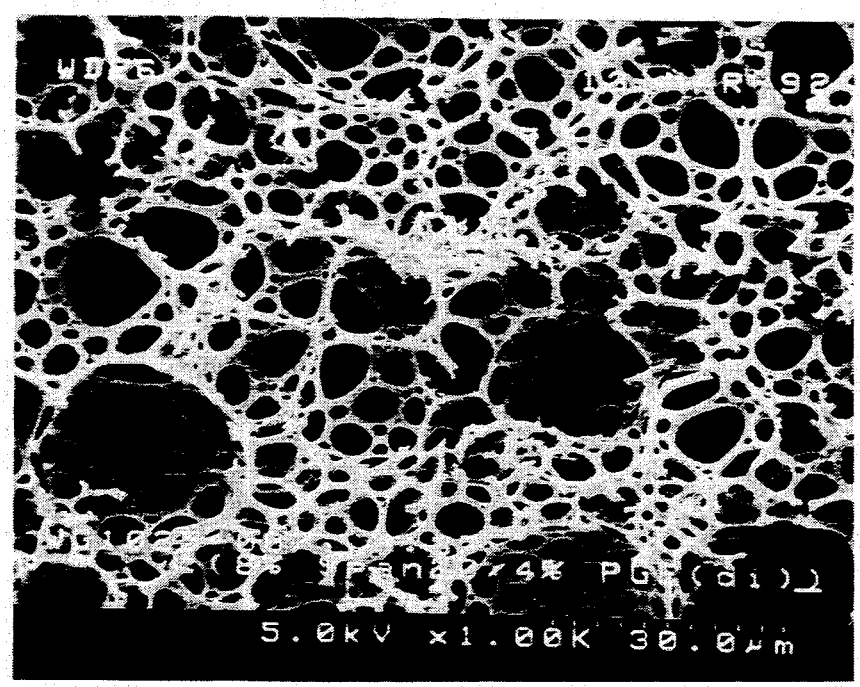
FIG. 4 of the drawings is a photomicrograph (1000X magnification) of a cut section of an absorbent polymeric foam according to the present invention that is prepared from a HIPE emulsion containing a preferred co-emulsifier system.

FIG. 4 is a photomicrograph (1000X magnification) that shows a representative polymeric foam prepared from a HIPE emulsion using a SPAN ® 20/PGE co-emulsifier system like that of this example. The foam structure shown in FIG. 4 is in its expanded state. As can be seen, this foam structure has relatively small pores of relatively uniform size, i.e. the foam structure is relatively homogeneous. This suggests evidence of reduced coalescence of the water droplets during curing of the HIPE emulsion.

EXAMPLE IV B

A water phase containing calcium chloride/potassium persulfate and an oil phase monomer mixture containing SPAN ® 20 are prepared as in Example IV A. A half-size batch monomer mixture is also prepared by adding a PGE emulsifier that imparts a minimum oil/water IFT of 0.22 dynes/cm. This PGE is obtained by esterifying polyglycerols with fatty acids in a weight ratio of about 67:33 using reaction conditions similar to those described in Example IV A. The composition of the polyglycerols and fatty acids used in making the PGE are shown in the following table:

|  | Wt. % |
| --- | --- |
| Polyglycerols |  |
| linear diglycerols | 73.1 |
| triglycerol or higher | 24.5 |
| cyclic diglycerols | 2.4 |
| Fatty Acids |  |
| C8 | — |
| C10 | — |
| C12 | 32 |
| C14 | 37 |
| C16 | 11 |
| C18:0 | 3.2 |
| C18:1 | 13 |
| C18:2 | 1.5 |

After mixing, each oil phase batch is allowed to settle overnight with the supernatants being withdrawn and mixed at a ratio of 2 parts of the SPAN ® 20 containing oil phase to 1 part PGE containing oil phase, as in Example IV A. The aqueous and oil phases are then fed to the combined dynamic and static mixer apparatus as in Example IV A. The combined apparatus is filled with the oil and water phases at a ratio of 2 parts water to 1 part oil, while venting the apparatus to allow air to escape until filling of the apparatus is complete. The flow rates during filling are 3.0 g/sec oil phase and 7.5 cc/sec water phase.

Once the apparatus is filled, agitation is begun, with the impeller turning at 1200 RPM. The aqueous phase flow rate is then evenly ramped up to 45.0 cc/sec and the oil phase flow rate is evenly ramped down to 1.66 g/sec over a time period of 60 sec. The impeller RPM is then lowered to 1100 evenly over a period of 30 sec and then instantly increased to 1800 RPM. The water phase flow rate is then adjusted to 47.6 cc/sec. The back pressure is 5.3 psi. The formed emulsion is collected in molds and then kept in a room maintained at 65° C. for 18 hours to allow for curing, as in Example IV A. The cured foams are washed with a 1% calcium chloride solution. The residual solution retained in the foam before drying is 5 times the weight of foam.

EXAMPLE IV C

A water phase containing calcium chloride/potassium persulfate and an oil phase monomer mixture containing SPAN® 20 are prepared as in Example IV A. A half-size batch monomer mixture is also prepared by adding a PGE emulsifier that imparts a minimum oil/water IFT of 0.08 dynes/cm. This PGE is obtained by esterifying polyglycerols with fatty acids in a weight ratio of about 67:33 using reaction conditions similar to those described in Example IV A. The composition of the polyglycerols and fatty acids used in making the PGE are shown in the following table:

|  | Wt. % |
|---|---|
| Polyglycerols | |
| linear diglycerols | ~71 |
| triglycerol or higher | ~24 |
| cyclic diglycerols | ~5 |
| Fatty Acids | |
| C8 | — |
| C10 | 4.4 |
| C12 | 43.6 |
| C14 | 25.1 |
| C16 | 12.1 |
| C18:0 | 3.8 |
| C18:1 | 9.2 |
| C18:2 | 1.4 |

After mixing, each oil phase batch is allowed to settle overnight with the supernatants being withdrawn and mixed at a ratio of 2 parts of the SPAN® 20 containing oil phase to 1 part PGE containing oil phase, as in Example IV A. The aqueous (45°–47° C.) and oil phases are then fed to the combined dynamic and static mixer apparatus as in Example IV A. The combined apparatus is filled with the oil and water phases at a ratio of 2 parts water to 1 part oil, while venting the apparatus to allow air to escape until filling of the apparatus is complete. The flow rates during filling are 2.2 g/sec oil phase and 4.7 cc/sec water phase.

Once the apparatus is filled, agitation is begun, with the impeller turning at 1800 RPM. The aqueous phase flow rate is then evenly ramped up to 45.5 cc/sec and the oil phase flow rate is evenly ramped down to 1.59 g/sec over a time period of 90 sec. The back pressure is 5.4 psi. The HIPE emulsion is collected in molds and then kept in a room maintained at 65° C. for 18 hours to allow for curing, as in Example IV A. The cured foams are washed with a 1% calcium chloride solution. The residual solution retained in the foam before drying is 5 times the weight of foam.

EXAMPLE IV D

A water phase containing calcium chloride/potassium persulfate and an oil phase monomer mixture containing SPAN® 20 are prepared as in Example IV A. A half-size batch monomer mixture is also prepared by adding a PGE emulsifier that imparts a minimum oil/water IFT of 0.013 dynes/cm. This PGE is obtained by esterifying polyglycerols with fatty acids in a weight ratio of about 61:39 using reaction conditions similar to those described in Example IV A. The composition of the polyglycerols and fatty acids used in making the PGE are shown in the following table:

|  | Wt. % |
|---|---|
| Polyglycerols | |
| linear diglycerols | ~15 |
| triglycerol or higher | ~85 |
| cyclic diglycerols | — |
| Fatty Acids | |
| C8 | 6 |
| C10 | 5 |
| C12 | 55 |
| C14 | 23 |
| C16 | 6 |
| C18:0 | 3 |
| C18:1 | 1 |
| C18:2 | 1 |

After mixing, each oil phase batch is allowed to settle overnight with the supernatants being withdrawn and mixed at a ratio of 2 parts of the SPAN® 20 containing oil phase to 1 part PGE containing oil phase, as in Example IV A. The aqueous (55°–60° C.) and oil phases are then fed to the combined dynamic and static mixer apparatus as in Example IV A. The combined apparatus is filled with the oil and water phases at a ratio of 2 parts water to 1 part oil, while venting the apparatus to allow air to escape until filling of the apparatus is complete. The flow rates during filling are 3.0 g/sec oil phase and 6.0 cc/sec water phase.

Once the apparatus is filled, agitation is begun, with the impeller turning at 1800 RPM. The aqueous phase flow rate is then evenly ramped up to 45.7 cc/sec and the oil phase flow rate is evenly ramped down to 1.58 g/sec over a time period of 120 sec. The back pressure is 5.4 psi. The HIPE emulsion is collected in molds and then kept in a room maintained at 65° C. for 18 hours to allow for curing, as in Example IV A. The cured foams are washed with a 1% calcium chloride solution. The residual solution retained in the foam before drying is 5 times the weight of foam.

EXAMPLE IV E

A water phase containing calcium chloride/potassium persulfate and an oil phase monomer mixture containing SPAN® 20 are prepared as in Example IV A. A half-size batch monomer mixture is also prepared by adding a PGE emulsifier that imparts a minimum oil/water IFT of 0.042 dynes/cm. This PGE is obtained by esterifying polyglycerols with fatty acids in a weight ratio of about 67:33 using reaction conditions similar to those described in Example IV A. The composition of the polyglycerols and fatty acids used in making the PGE are shown in the following table:

|  | Wt. % |
| --- | --- |
| Polyglycerols | |
| linear diglycerols | 70.6 |
| triglycerol or higher | 24.1 |
| cyclic diglycerols | 5.3 |
| Fatty Acids | |
| C8 | — |
| C10 | — |
| C12 | 32.1 |
| C14 | 38.6 |
| C16 | 11 |
| C18:0 | 3.2 |
| C18:1 | 13.4 |
| C18:2 | 1.4 |

After mixing, each oil phase batch is allowed to settle overnight with the supernatants being withdrawn and mixed at a ratio of 2 parts of the SPAN ® 20 containing oil phase to 1 part PGE containing oil phase, as in Example IV A. The aqueous and oil phases are then fed to the combined dynamic and static mixer apparatus as in Example IV A. The combined apparatus is filled with the oil and water phases at a ratio of 2 parts water to 1 part oil, while venting the apparatus to allow air to escape until filling of the apparatus is complete. The flow rates during filling are 1.7 g/sec oil phase and 3.0 cc/sec water phase.

Once the apparatus is filled, agitation is begun, with the impeller turning at 1100 RPM. The aqueous phase flow rate is then evenly ramped up to 48.4 cc/sec. over a time period of 90 sec. The back pressure is 5.0 psi. The impeller RPM is then instantly increased to 1800 RPM. The back pressure increases to 5.8 psi. The HIPE emulsion is collected in molds and then kept in a room maintained at 65° C. for 18 hours to allow for curing, as in Example IV A. The cured foams are washed with a 1% calcium chloride solution. The residual solution retained in the foam before drying is 5 times the weight of foam.

EXAMPLE IV F

A water phase containing calcium chloride/potassium persulfate and an oil phase monomer mixture containing SPAN ® 20 are prepared as in Example IV A. To the monomer mixture is added sorbitan laurate (480 g as SPAN ® 20) and a mixture of sorbitan laurate (240 g) and sorbitan palmitate (240 g as SPAN ® 40). After mixing, the oil phase is allowed to settle overnight, with the supernatant being withdrawn for use in forming the HIPE emulsion.

The aqueous (48°–50° C.) and oil phases are then fed to the combined dynamic and static mixer apparatus as in Example IV A. The combined apparatus is filled with the oil and water phases at a ratio of 2 parts water to 1 part oil, while venting the apparatus to allow air to escape until filling of the apparatus is complete. The flow rates during filling are 3.0 g/sec oil phase and 6 cc/sec water phase.

Once the apparatus is filled, agitation is begun, with the impeller turning at 1800 RPM. The aqueous phase flow rate is then evenly ramped up to 42.3 cc/sec and the oil phase flow rate is evenly ramped down to 1.5 g/sec over a time period of 60 sec. The back pressure is 4.5 psi. The HIPE emulsion is collected in molds (round tubs with a central core) and then kept in a room maintained at 65° C. for 18 hours to allow for curing, as in Example IV A. The cured foams are washed with a 1% calcium chloride solution. The residual solution retained in the foam before drying is 5 times the weight of foam.

What is claimed is:

1. A collapsed polymeric foam material which, upon contact with aqueous body fluids, expands and absorbs said fluids, said polymeric foam material comprising a hydrophilic, flexible, nonionic polymeric foam structure of interconnected open cells, which foam structure has:

A) a specific surface area per foam volume of at least about 0.025 $m^2$/cc;
   B) at least about 0.1% by weight of said polymeric foam material of a toxicologically acceptable hygroscopic, hydrated salt incorporated therein:
   C) in its collapsed state, an expansion pressure of about 30 kPa or less; and
   D) in its expanded state, a density when saturated at 88° F. (31.1° C.) to its free absorbent capacity with synthetic urine having a surface tension of 65±5 dynes/cm of from about 10 to about 50% of its dry basis density in its collapsed state.

2. The foam material of claim 1 wherein said specific surface area per foam volume of at least about 0.05 $m^2$/cc and a residual water content of at least about 4% by weight of the foam material in its collapsed state.

3. The foam material of claim 2 wherein said foam structure has:

A) a capillary suction specific surface area of from about 0.7 to about 8 $m^2$/g;
   B) from about 0.1 to about 8% by weight of the foam material of calcium chloride, and from about 0.5 to about 20% by weight of the foam material a nonionic oil-soluble enmlsifier incorporated therein to render the surface of the foam structure hydrophilic;
   C) in its collapsed state:
      (i) a residual water content of from about 4 to about 30% by weight of the foam material;
      (ii) a dry basis density of from about 0.05 to about 0.4 g/$cm^3$.
   D) in its expanded state:
      (i) a pore volume of from about 12 to about 100 mL/g;
      (ii) a resistance to compression deflection of from about 2 to about 80% when saturated at 88° F. (31.1° C.) to its free absorbent capacity with synthetic urine having a surface tension of 65±5 dynes/cm;
      (iii) a number average cell size of from about 5 to about 50 microns.

4. The foam material of claim 3 wherein said foam structure has:

A) said capillary suction specific surface area is from about 1.5 to about 6 $m^2$/g;
   B) said weight percent range of calcium chloride is from about 3 to about 6% by weight of the foam material and from about 5 to about 12% by weight of the foam material sorbitan laurate incorporated therein;
   C) in the collapsed state:
      (i) said residual water content is from about 5 to about 15% by weight of the foam material;
      (ii) said dry basis density is from about 0.1 to about 0.2 g/$cm^3$;
      (iii) said expansion pressure is from about 7 to about 20 kPa;
   D) in said expanded state:

(i) said pore volume is from about 25 to about 50 mL/g;

(ii) said resistance to compression deflection is from about 5 to about 40%;

(iii) said number average cell size is from about 5 to about 35 microns;

(iv) said density when saturated with said synthetic urine is from about 10 to about 30% of its dry basis density in its collapsed state.

5. The foam material of claim 1 comprises a polymerized water-in-oil emulsion having:
1) an oil phase comprising:
   a) from about 67 to about 98% by weight of a monomer component comprising:
      i) from about 5 to about 40% by weight of a substantially water-insoluble, monofunctional glassy monomer;
      ii) from about 30 to about 80% by weight of a substantially water-insoluble, monofunctional rubbery comonomer;
      iii) from about 10 to about 40% by weight of a substantially water-insoluble, polyfunctional crosslinking agent; and
   b) from about 2 to about 33% by weight of an emulsifier component which is soluble in the oil phase and which forms a stable water-in-oil emulsion; and
2) a water phase comprising from about 0.2 to about 20% by weight of a water-soluble electrolyte;
3) a weight ratio of water phase to oil phase of from about 12:1 to about 100:1.

6. The foam material of claim 5 wherein:
1) the oil phase comprises:
   a) from about 80 to about 95% by weight monomer component comprising:
      i) from about 10 to about 30% by weight glassy monomer selected from the group consisting of styrene-based monomers and methacrylate-based monomers;
      ii) from about 50 to about 70% by weight rubbery comonomer selected from the group consisting of n-butylacrylate and 2-ethylhexylacrylate;
      iii) from about 15 to about 25% by weight divinylbenzene;
   b) from about 5 to about 20% by weight emulsifier component comprising sorbitan laurate;
2) the water phase comprises from about 1 to about 10% by weight calcium chloride;
3) the weight ratio of water phase to oil phase is from about 20:1 to about 70:1.

7. The foam material of claim 6 wherein said monomer component comprises:
   i) from about 15 to about 25% by weight styrene;
   ii) from about 55 to about 65% by weight 2-ethylhexylacrylate;
   iii) from about 15 to about 25% by weight divinylbenzene.

8. An absorbera article especially suitable for absorbing and retaining aqueous body fluids and having a fluid discharge region, said article comprising:
I) a backing sheet; and
II) an absorbent core positioned between said backing sheet and the fluid discharge region of the article, said absorbent core comprising the foam material of claim 1.

9. The absorbent article of claim 8 wherein the foam material has:

a) a free absorbent capacity at 88° F. (31.1° C.) of at least about 12 mL of said synthetic urine, per gram of dry foam material; and
b) a vertical wicking rate at 37° C. such that said synthetic urine wicks along a 5 cm vertical length of the foam material in 30 minutes or less.

10. The absorbent article of claim 9 wherein the foam material has:
a) said free absorbent capacity is at least about 20 mL of said synthetic urine, per gram of dry foam material;
b) said vertical wicking rate is such that said synthetic urine wicks along said vertical length in 5 minutes or less: and
c) a vertical wicking absorbent capacity at 37° C. of at least about 75% of said free absorbent capacity at a vertical wicking height of 11.4 cm.

11. The absorbent article of claim 9 wherein said absorbent core comprises: (1) a fluid-handling layer positioned in said fluid discharge region; and (2) a fluid storage/redistribution layer in fluid communication with said fluid-handling layer and comprising the foam material.

12. The absorbent article of claim 11 wherein said fluid-handling layer is a fluid acquisition/distribution layer comprising cellulosic fibers.

13. The absorbent article of claim 12 wherein said cellulosic fibers comprise chemically stiffened cellulosic fibers.

14. The absorbent article of claim 12 wherein said storage/redistribution layer underlies said acquisition/distribution layer.

15. The absorbent article of claim 14 wherein said backing sheet is liquid impervious and which additionally comprises a liquid pervious topsheet joined with said backing sheet, said absorbent core being positioned between said topsheet and said backing sheet.

16. The absorbent article of claim 15 which is a diaper.

17. A diaper article useful for absorbing aqueous body fluids discharged by an incontinent individual and having a fluid discharge region, said diaper article comprising:
I) a liquid-impervious backing sheet;
II) a liquid-pervious topsheet;
III) an absorbent core positioned between said backing sheet and said top sheet, said absorbent core comprising a collapsed polymeric foam material which, upon contact with aqueous body fluids, expands and absorbs said fluids, said polymeric foam material comprising a hydrophilic, flexible, nonionic polymeric foam structure of interconnected open cells, which foam structure has:
   A) a capillary suction specific surface area of from about 1.5 to about 6 $m^2/g$;
   B) from about 3 to about 6% by weight of said polymeric foam material of calcium chloride and from about 5 to about 12% by weight of said polymeric foam material of sorbitan laurate incorporated therein;
   C) in its collapsed state:
      (i) a residual water content of from about 5 to about 15% by weight of said polymeric foam material;
      (ii) a dry basis density of from about 0.1 to about 0.2 $g/cm^3$;
      (iii) an expansion pressure of from about 7 to about 20 kPa;

D) in its expanded state:
  (i) a pore volume of from about 25 to about 50 mL/g;
  (ii) a resistance to compression deflection of from about 5 to about 40%;
  (iii) a number average cell size of from about 5 to about 35 microns;
  (iv) a density when saturated at 88° F. (31.1° C.) to its free absorbent capacity with synthetic urine having a surface tension of 65±5 dynes/cm of from about 10 to about 30% of its dry basis density in its collapsed state.

18. The diaper article of claim 17 wherein said foam material has:
  a) a free absorbent capacity at 88° F. (31.1° C.) of at least about 20 mL of said synthetic urine, per gram of dry foam material;
  b) a vertical wicking rate at 37° C. such that said synthetic urine wicks along a 5 cm vertical length of said foam material in 5 minutes or less; and
  c) a vertical wicking absorbent capacity at 37° C. of at least about 75% of said free absorbent capacity at a vertical wicking height of 11.4 cm.

19. The diaper article of claim 18 wherein said absorbent core comprises: (1) an upper fluid-handling layer positioned in the fluid discharge region of the wearer of the diaper article; and (2) a lower fluid storage/redistribution layer in fluid communication with said upper layer and comprising said foam material.

20. The diaper article of claim 19 wherein said upper layer is a fluid acquisition/distribution layer comprising cellulosic fibers.

21. The diaper article of claim 20 wherein said cellulosic fibers comprise chemically stiffened cellulosic fibers.

22. The diaper article of claim 18 wherein said foam material comprises a polymerized water-in-oil emulsion having:
  1) an oil phase comprising:
    a) from about 80 to about 95% by weight of a monomer component comprising:
      i) from about 10 to about 30% by weight substantially water-insoluble monofunctional glassy monomer selected from the group consisting of styrene-based monomers and methacrylate-based monomers;
      ii) from about 50 to about 70% by weight substantially water-insoluble, monofunctional rubbery comonomer selected from the group consisting of n-butylacrylate and 2-ethylhexylacrylate;
      iii) from about 15 to about 25% by weight divinylbenzene;
    b) from about 5 to about 20% by weight of an emulsifier component comprising sorbitan laurate which is soluble in the oil phase and which forms a stable water-in-oil emulsion;
  2) a water phase comprising from about 1 to about 10% by weight calcium chloride;
  3) a weight ratio of water phase to oil phase of from about 25:1 to about 50: 1.

23. The diaper article of claim 22 wherein said monomer component comprises:
  i) from about 15 to about 25% by weight styrene;
  ii) from about 55 to about 65% by weight 2-ethylhexylacrylate;
  iii) from about 15 to about 25% by weight divinylbenzene.

* * * * *

UNITED STATES PATENT AND TRADEMARK OFFICE
CERTIFICATE OF CORRECTION

PATENT NO. : 5,387,207
DATED : 2/07/95
INVENTOR(S) : J. C. Dyer et al.

It is certified that error appears in the above-identified patent and that said Letters Patent is hereby corrected as shown below:

In Col. 4, line 34, "water-insoluble." should read --water-insoluble,--.

In Col. 13, line 30, "density," should read --density.--.

In Col. 13, line 54, "Compression" should read --compression--.

In Col. 16, line 67, "VEST" should read --TEST--.

In Col. 19, line 46, "monomers." should read --monomers,--.

In Col. 25, line 10, "emulsifiers." should read --emulsifiers,--.

In Col. 26, line 5, "i.e.." should read --i.e.,--.

In Col. 34, line 48, "Foam" should read --foam--.

In Col. 42, line 3, "(500X" should read --(500 X--.

In Col. 44, line 24, "(1000X" should read --(1000 X--.

In Col. 49, line 59, "absorbera" should read --absorbent--.

Signed and Sealed this

Twenty-eighth Day of April, 1998

*Attest:*

BRUCE LEHMAN

*Attesting Officer*     *Commissioner of Patents and Trademarks*